United States Patent
Mihalcea et al.

(10) Patent No.: US 12,365,993 B2
(45) Date of Patent: Jul. 22, 2025

(54) PROCESS FOR IMPROVING CARBON CONVERSION EFFICIENCY

(71) Applicant: LanzaTech, Inc., Skokie, IL (US)

(72) Inventors: Christophe Mihalcea, Chicago, IL (US); Robert Conrado, Washington, DC (US); Nicholas Bourdakos, Toronto (CA); Xueliang Li, Morton Grove, IL (US); Sean Simpson, Evanston, IL (US)

(73) Assignee: LanzaTech, Inc., Skokie, IL (US)

( * ) Notice: Subject to any disclaimer, the term of this patent is extended or adjusted under 35 U.S.C. 154(b) by 575 days.

(21) Appl. No.: 17/805,223

(22) Filed: Jun. 2, 2022

(65) Prior Publication Data
US 2022/0298649 A1  Sep. 22, 2022

Related U.S. Application Data

(63) Continuation of application No. 16/273,933, filed on Feb. 12, 2019, now Pat. No. 11,359,294.
(Continued)

(51) Int. Cl.
*C25B 1/02* (2006.01)
*B01D 53/62* (2006.01)
(Continued)

(52) U.S. Cl.
CPC .............. *C25B 1/02* (2013.01); *B01D 53/62* (2013.01); *C12P 1/04* (2013.01); *C25B 1/00* (2013.01);
(Continued)

(58) Field of Classification Search
CPC ...... C12P 1/00; C12P 1/04; C12P 7/00; C12P 7/02; C12P 7/18; C12P 7/20; C12P 7/22; C25B 1/04; C25B 1/23
See application file for complete search history.

(56) References Cited

U.S. PATENT DOCUMENTS

2010/0317074 A1* 12/2010 Simpson ................ C12P 7/08
435/140
2011/0114502 A1* 5/2011 Cole ...................... C25B 1/55
205/450
(Continued)

FOREIGN PATENT DOCUMENTS

CN        102834163 A    12/2012
CN        103140606 A    6/2013
(Continued)

OTHER PUBLICATIONS

Arkansas Univ. "High pressure synthesis gas fermentation, Jan. 15, 1991-Apr. 14, 1991.", Jan. 1991. https://doi.org/10.2172/7270080 (Year: 1981).*

*Primary Examiner* — Kaj K Olsen

(57) ABSTRACT

The invention provides for the integration of a CO-consuming process, such as a gas fermentation process, with a $CO_2$ electrolysis process. The invention is capable of utilizing a $CO_2$-comprising gaseous substrate generated by an industrial process and provides for one or more removal modules to remove at least one constituent from a $CO_2$-comprising gaseous substrate prior to passage of the gaseous substrate to a $CO_2$ electrolysis module. The invention may further comprise one or more pressure modules, one or more $CO_2$ concentration modules, one or more $O_2$ separation modules, and/or an $H_2$ electrolysis module. Carbon conversion efficiency is increased by recycling $CO_2$ produced by a CO-consuming process to the $CO_2$ electrolysis process.

13 Claims, 8 Drawing Sheets

Related U.S. Application Data

(60) Provisional application No. 62/629,163, filed on Feb. 12, 2018.

(51) Int. Cl.
 *C12P 1/04* (2006.01)
 *C25B 1/00* (2021.01)
 *C25B 1/04* (2021.01)
 *C25B 1/23* (2021.01)
 *C25B 15/08* (2006.01)

(52) U.S. Cl.
 CPC ............... *C25B 1/04* (2013.01); *C25B 1/23* (2021.01); *C25B 15/08* (2013.01); *B01D 2257/50* (2013.01); *B01D 2257/502* (2013.01); *B01D 2257/504* (2013.01); *B01J 2231/625* (2013.01); *Y02C 20/40* (2020.08)

(56) References Cited

U.S. PATENT DOCUMENTS

| | | | |
|---|---|---|---|
| 2013/0149755 A1* | 6/2013 | Reed | C12P 7/6463 204/278 |
| 2013/0175181 A1* | 7/2013 | Kaczur | C25B 3/23 205/345 |
| 2015/0064512 A1* | 3/2015 | Turney | H01M 10/34 429/50 |
| 2015/0152441 A1* | 6/2015 | Schultz | B01D 53/0462 435/163 |

FOREIGN PATENT DOCUMENTS

| | | |
|---|---|---|
| CN | 104024479 A | 9/2014 |
| EP | 3222731 A1 * | 9/2017 |

* cited by examiner

PROCESS FOR IMPROVING CARBON CONVERSION EFFICIENCY

CROSS REFERENCE TO RELATED APPLICATIONS

This application is a continuation of U.S. patent application Ser. No. 16/273,933 filed Feb. 12, 2019, which claims the benefit of U.S. Provisional Patent Application No. 62/629,163 filed Feb. 12, 2018, the entirety of which are incorporated herein by reference.

FIELD OF THE INVENTION

The invention relates to processes and methods for improving carbon conversion efficiency. In particular, the invention relates to the combination of a carbon monoxide-consuming process with an industrial process, wherein gas from the industrial process undergoes treatment and conversion, and carbon dioxide produced by the carbon monoxide-consuming process is recycled to increase product yield.

BACKGROUND OF THE INVENTION

Carbon dioxide ($CO_2$) accounts for about 76% of global greenhouse gas emissions from human activities, with methane (16%), nitrous oxide (6%), and fluorinated gases (2%) accounting for the balance (United States Environmental Protection Agency). Reduction of greenhouse gas emissions, particularly $CO_2$, is critical to halt the progression of global warming and the accompanying shifts in climate and weather.

It has long been recognized that catalytic processes, such as the Fischer-Tropsch process, may be used to convert gases comprising $CO_2$, carbon monoxide (CO), and/or hydrogen ($H_2$) into a variety of fuels and chemicals. Recently, however, gas fermentation has emerged as an alternative platform for the biological fixation of such gases. In particular, C1-fixing microorganisms have been demonstrated to convert gases comprising $CO_2$, CO, $CH_4$, and/or $H_2$ into products such as ethanol and 2,3-butanediol.

Such gases may be derived, for example, from industrial processes, including gas emissions from carbohydrate fermentation, gas fermentation, cement making, pulp and paper making, steel making, oil refining and associated processes, petrochemical production, coke production, anaerobic or aerobic digestion, gasification, natural gas extraction, oil extraction, metallurgical processes, production and/or refinement of aluminum, copper, and/or ferroalloys, geological reservoirs, Fischer-Tropsch processes, methanol production, pyrolysis, steam methane reforming, dry methane reforming, partial oxidation of biogas or natural gas, and autothermal reforming of biogas or natural gas.

To optimize the usage of these gases in CO-consuming processes, such as C1-fixing fermentation processes, an industrial gas may require a combination of treatment and conversion. Accordingly, there remains a need for improved integration of industrial processes with CO-consuming processes, including processes for treatment and conversion of industrial gases, thereby optimizing carbon conversion efficiency.

BRIEF SUMMARY OF THE INVENTION

It is against the above background that the present invention provides certain advantages and advancements over the prior art.

Although this invention disclosed herein is not limited to specific advantages or functionalities, the invention provides a process for improving carbon conversion efficiency, wherein the process comprises passing a $CO_2$-comprising gaseous substrate from an industrial process to a first removal module for removal of at least one constituent from the $CO_2$-comprising gaseous substrate to produce a first $CO_2$-treated gas stream, passing the first $CO_2$-treated gas stream to a $CO_2$ electrolysis module for conversion of at least a portion of the first $CO_2$-treated gas stream to produce a CO-enriched stream and a first $O_2$-enriched stream, and passing at least a portion of the CO-enriched stream to a CO-consuming process.

In some aspects of the process described herein, the $CO_2$-comprising gaseous substrate from the industrial process is first passed to a pressure module to produce a pressurized $CO_2$-comprising gas stream, and the pressurized $CO_2$-comprising gas stream is passed to the first removal module.

In some aspects of the process described herein, the process further comprises one or more of passing at least a portion of the first $O_2$-enriched stream directly to the industrial process and passing at least a portion of the first $O_2$-enriched stream to an $O_2$ separation module to produce a second $O_2$-enriched stream and an $O_2$-lean stream.

In some aspects of the process described herein, the process further comprises one or more of passing at least of portion of the second $O_2$-enriched stream to the industrial process, passing at least of portion of the $O_2$-lean stream to the $CO_2$ electrolysis module, and passing at least of portion of the $O_2$-lean stream to the CO-consuming process.

In some aspects of the process described herein, the process further comprises passing at least a portion of the $CO_2$-comprising gaseous substrate from the industrial process and/or at least a portion of the first $CO_2$-treated gas stream to a first $CO_2$ concentration module to produce a first $CO_2$-concentrated stream and a first $CO_2$-lean stream.

In some aspects of the process described herein, the process further comprises passing at least a portion of the first $CO_2$-concentrated stream to one or more of the first removal module and the $CO_2$ electrolysis module.

In some aspects of the process described herein, the first $CO_2$-lean stream comprises CO and/or $H_2$, and the process further comprises passing at least a portion of the first $CO_2$-lean stream to the CO-consuming process.

In some aspects of the process described herein, the process comprises passing at least a portion of the CO-enriched stream to a pressure module to produce a pressurized CO-stream and passing at least a portion of the pressurized CO-stream to the CO-consuming process.

In some aspects of the process described herein, the process further comprises passing a water substrate to an $H_2$ electrolysis module to produce an $H_2$-enriched stream and passing at least a portion of the $H_2$-enriched stream to the CO-consuming process.

In some aspects of the process described herein, the CO-consuming process produces a tail gas comprising $CO_2$.

In some aspects of the process described herein, the process further comprises one or more of passing at least a portion of the tail gas comprising $CO_2$ to the first removal module or to a second removal module for removal of at least one constituent from the tail gas to produce a second $CO_2$-treated gas stream and passing at least a portion of the tail gas comprising $CO_2$ to a second $CO_2$ concentration module to produce a second $CO_2$-concentrated stream and a second $CO_2$-lean stream.

In some aspects of the process described herein, at least a portion of the tail gas comprising $CO_2$ is passed to a pressure module to produce a pressurized tail gas stream, and the pressurized tail gas stream is passed to the first removal module and/or the second removal module.

In some aspects of the process described herein, the process further comprises passing at least a portion of the second $CO_2$-concentrated stream to the first removal module or to the second removal module for removal of at least one constituent from the tail gas to produce a second $CO_2$-treated gas stream.

In some aspects of the process described herein, the process further comprises passing at least a portion of the second $CO_2$-treated gas stream to the $CO_2$ electrolysis module.

In some aspects of the process described herein, the $CO_2$-comprising gaseous substrate from the industrial process further comprises one or more of CO, $H_2$, and $CH_4$.

In some aspects of the process described herein, the industrial process is selected from the group comprising carbohydrate fermentation, gas fermentation, cement making, pulp and paper making, steel making, oil refining and associated processes, petrochemical production, coke production, anaerobic or aerobic digestion, gasification, natural gas extraction, oil extraction, metallurgical processes, production and/or refinement of aluminum, copper, and/or ferroalloys, geological reservoirs, Fischer-Tropsch processes, methanol production, pyrolysis, steam methane reforming, dry methane reforming, partial oxidation of biogas or natural gas, and autothermal reforming of biogas or natural gas.

In some aspects of the process described herein, the $CO_2$-comprising gaseous substrate is derived from a blend of at least two or more sources.

In some aspects of the process described herein, the first removal module is selected from the group consisting of a hydrolysis module, an acid gas removal module, a deoxygenation module, a catalytic hydrogenation module, a particulate removal module, a chloride removal module, a tar removal module, and a hydrogen cyanide polishing module.

In some aspects of the process described herein, at least one constituent removed from the $CO_2$-comprising gas substrate is selected from the group consisting of sulfur compounds, aromatic compounds, alkynes, alkenes, alkanes, olefins, nitrogen compounds, oxygen, phosphorous-comprising compounds, particulate matter, solids, oxygen, halogenated compounds, silicon-comprising compounds, carbonyls, metals, alcohols, esters, ketones, peroxides, aldehydes, ethers, tars, and naphthalene.

In some aspects of the process described herein, the CO-consuming process is a fermentation process comprising a culture of at least one carboxydotrophic microorganism. The carboxydotrophic microorganism may be a carboxydotrophic bacterium.

In some aspects of the process described herein, the carboxydotrophic bacterium is selected from the group comprising *Moorella*, *Clostridium*, *Ruminococcus*, *Acetobacterium*, *Eubacterium*, *Butyribacterium*, *Oxobacter*, *Methanosarcina*, and *Desulfotomaculum*. In some aspects of the process described herein, the carboxydotrophic bacterium is *Clostridium autoethanogenum*.

In some aspects of the process described herein, the fermentation process produces a fermentation product selected from the group consisting of ethanol, butyrate, 2,3-butanediol, lactate, butene, butadiene, methyl ethyl ketone, ethylene, acetone, isopropanol, lipids, 3-hydroypropionate, terpenes, fatty acids, 2-butanol, 1,2-propanediol, and 1-propanol.

BRIEF DESCRIPTION OF THE DRAWINGS

FIG. 1B further shows a pressure module prior to a removal module.

FIG. 1C further shows a pressure module prior to a CO-consuming process.

DETAILED DESCRIPTION OF THE INVENTION

Figure 1A:
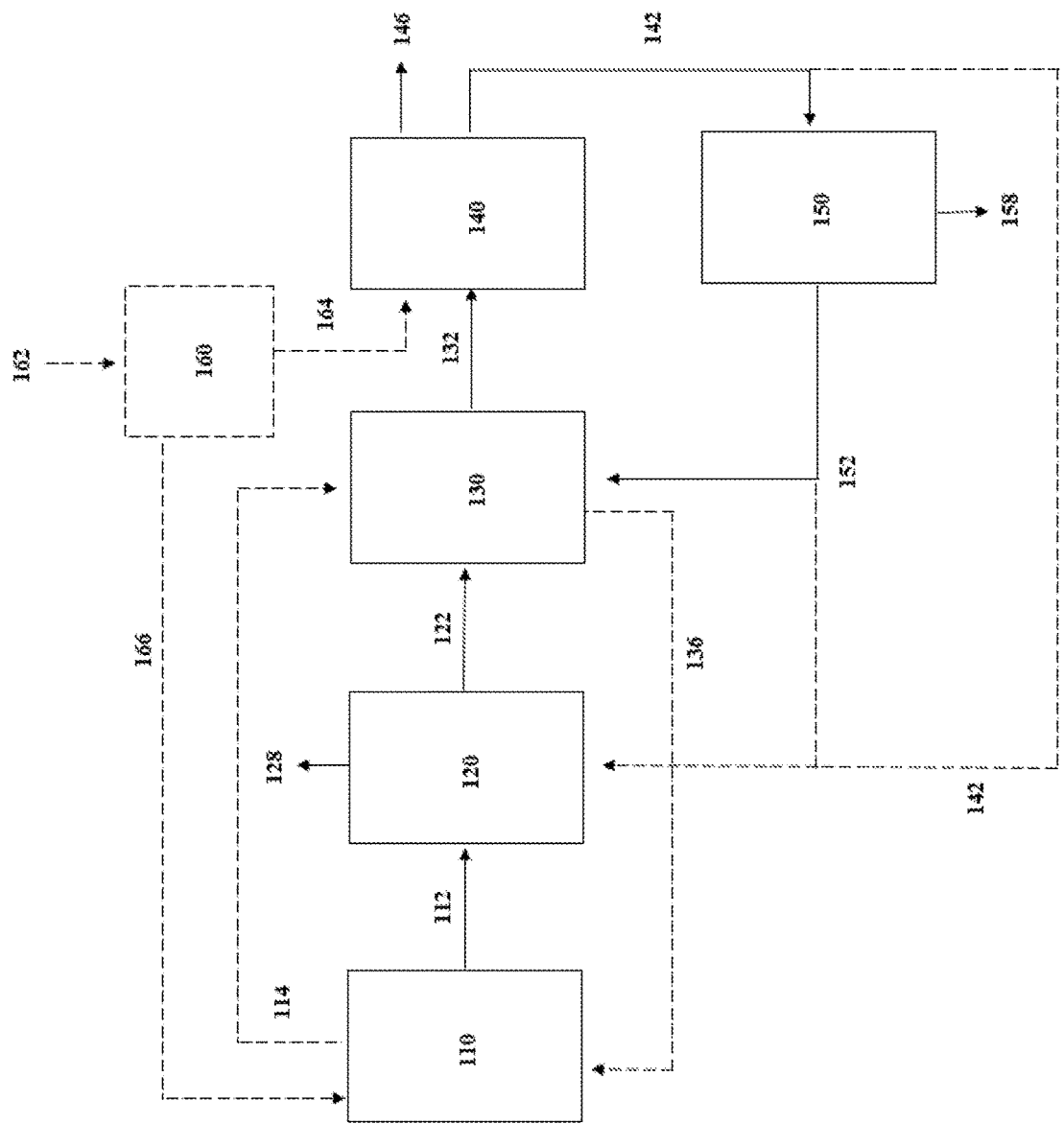
FIGS. 1A, 1B, and 1C show a process integration scheme depicting integration of a removal module, a $CO_2$ electrolysis module, and an optional $H_2$ electrolysis module with a CO-consuming process.

The inventors have identified that the integration of a $CO_2$-generating industrial process with a CO-consuming process, as well as a removal process prior to a $CO_2$ electrolysis process, is capable of providing substantial benefits to the $CO_2$-generating industrial process and the CO-consuming process, which may be a C1-fixing fermentation process.

The term "industrial process" refers to a process for producing, converting, refining, reforming, extracting, or oxidizing a substance involving chemical, physical, electrical, and/or mechanical steps. Exemplary industrial processes include, but are not limited to, carbohydrate fermentation, gas fermentation, cement making, pulp and paper making, steel making, oil refining and associated processes, petrochemical production, coke production, anaerobic or aerobic digestion, gasification (such as gasification of biomass, liquid waste streams, solid waste streams, municipal streams, fossil resources including natural gas, coal and oil), natural gas extraction, oil extraction, metallurgical processes, production and/or refinement of aluminum, copper, and/or ferroalloys, geological reservoirs, Fischer-Tropsch processes, methanol production, pyrolysis, steam methane reforming, dry methane reforming, partial oxidation of biogas or natural gas, and autothermal reforming of biogas or natural gas. In these embodiments, the substrate and/or C1-carbon source may be captured from the industrial process before it is emitted into the atmosphere, using any convenient method.

The terms "gas from an industrial process," "gas source from an industrial process," and "gaseous substrate from an industrial process" can be used interchangeably to refer to an off-gas from an industrial process, a by-product of an industrial process, a co-product of an industrial process, a gas recycled within an industrial process, and/or a gas used within an industrial facility for energy recovery. In some embodiments, a gas from an industrial process is a pressure swing adsorption (PSA) tail gas. In some embodiments, a gas from an industrial process is a gas obtained through a $CO_2$ extraction process, which may involve amine scrubbing or use of a carbonic anhydrase solution.

"C1" refers to a one-carbon molecule, for example, CO, $CO_2$, methane ($CH_4$), or methanol ($CH_3OH$). "C1-oxygenate" refers to a one-carbon molecule that also comprises at least one oxygen atom, for example, CO, $CO_2$, or $CH_3OH$. "C1-carbon source" refers a one carbon-molecule that serves as a partial or sole carbon source for a microorganism of the invention. For example, a C1-carbon source may comprise one or more of CO, $CO_2$, $CH_4$, $CH_3OH$, or formic acid ($CH_2O_2$). Preferably, a C1-carbon source comprises one or both of CO and $CO_2$. A "C1-fixing microorganism" is a microorganism that has the ability to produce one or more products from a C1-carbon source. Typically, a microorganism of the invention is a C1-fixing bacterium.

"Substrate" refers to a carbon and/or energy source. Typically, the substrate is gaseous and comprises a C1-carbon source, for example, CO, $CO_2$, and/or $CH_4$. Preferably, the substrate comprises a C1-carbon source of CO or CO and $CO_2$. The substrate may further comprise other non-carbon components, such as $H_2$, $N_2$, or electrons. As used herein, "substrate" may refer to a carbon and/or energy source for a microorganism of the invention.

The term "co-substrate" refers to a substance that, while not necessarily being the primary energy and material source for product synthesis, can be utilised for product synthesis when combined with another substrate, such as the primary substrate.

A "$CO_2$-comprising gaseous substrate," "$CO_2$-comprising gas," or "$CO_2$-comprising gaseous source" may include any gas that comprises $CO_2$. The gaseous substrate will typically comprise a significant proportion of $CO_2$, preferably at least about 5% to about 100% $CO_2$ by volume. Additionally, the gaseous substrate may comprise one or more of hydrogen ($H_2$), oxygen ($O_2$), nitrogen ($N_2$), and/or $CH_4$. As used herein, CO, $H_2$, and $CH_4$ may be referred to as "energy-rich gases."

The term "carbon capture" as used herein refers to the sequestration of carbon compounds including $CO_2$ and/or CO from a stream comprising $CO_2$ and/or CO and either a) converting the $CO_2$ and/or CO into products, b) converting the $CO_2$ and/or CO into substances suitable for long term storage, c) trapping the $CO_2$ and/or CO in substances suitable for long term storage, or d) a combination of these processes.

The terms "increasing the efficiency," "increased efficiency," and the like refer to an increase in the rate and/or output of a reaction, such as an increased rate of converting the $CO_2$ and/or CO into products and/or an increased product concentration. When used in relation to a fermentation process, "increasing the efficiency" includes, but is not limited to, increasing one or more of the rate of growth of microorganisms catalysing a fermentation, the growth and/or product production rate at elevated product concentrations, the volume of desired product produced per volume of substrate consumed, the rate of production or level of production of the desired product, and the relative proportion of the desired product produced compared with other by-products of the fermentation.

"Reactant" as used herein refers to a substance that is present in a chemical reaction and is consumed during the reaction to produce a product. A reactant is a starting material that undergoes a change during a chemical reaction. In particular embodiments, a reactant includes, but is not limited to, CO and/or $H_2$. In particular embodiments, a reactant is $CO_2$.

A "CO-consuming process" refers to a process wherein CO is a reactant; CO is consumed to produce a product. A non-limiting example of a CO-consuming process is a C1-fixing gas fermentation process. A CO-consuming process may involve a $CO_2$-producing reaction. For example, a CO-consuming process may result in the production of at least one product, such as a fermentation product, as well as $CO_2$. In another example, acetic acid production is a CO-consuming process, wherein CO is reacted with methanol under pressure.

"Gas stream" refers to any stream of substrate which is capable of being passed, for example, from one module to another, from one module to a CO-consuming process, and/or from one module to a carbon capture means.

Gas streams typically will not be a pure $CO_2$ stream and will comprise proportions of at least one other component. For instance, each source may have differing proportions of $CO_2$, CO, $H_2$, and various constituents. Due to the varying proportions, a gas stream must be processed prior to being introduced to a CO-consuming process. Processing of the gas stream includes the removal and/or conversion of various constituents that may be microbe inhibitors and/or catalyst inhibitors. Preferably, catalyst inhibitors are removed and/or converted prior to being passed to an electrolysis module, and microbe inhibitors are removed and/or converted prior to being passed to a CO-consuming process. Additionally, a gas stream may need to undergo one or more concentration steps whereby the concentration of CO and/or $CO_2$ is increased. Preferably, a gas stream will undergo a concentration step to increase the concentration of $CO_2$ prior to being passed to the electrolysis module. It has been found that higher concentrations of $CO_2$ being passing into the electrolysis module results in higher concentrations of CO coming out of the electrolysis module.

"Removal module," "contaminant removal module," "clean-up module," "processing module," and the like include technologies that are capable of either converting and/or removing at least one constituent from a gas stream. Non-limiting examples of removal modules include hydrolysis modules, acid gas removal modules, deoxygenation modules, catalytic hydrogenation modules, particulate removal modules, chloride removal modules, tar removal modules, and hydrogen cyanide polishing modules.

The terms "constituents," "contaminants," and the like, as used herein, refer to the microbe inhibitors and/or catalyst inhibitors that may be found in a gas stream. In particular embodiments, the constituents include, but are not limited to, sulfur compounds, aromatic compounds, alkynes, alkenes, alkanes, olefins, nitrogen compounds, phosphorous-comprising compounds, particulate matter, solids, oxygen, halogenated compounds, silicon-comprising compounds, carbonyls, metals, alcohols, esters, ketones, peroxides, aldehydes, ethers, tars, and napthalene. Preferably, the constituent removed by the removal module does not include $CO_2$.

"Microbe inhibitors" as used herein refer to one or more constituents that slow down or prevent a particular chemical reaction or other process, including the microbe. In particular embodiments, the microbe inhibitors include, but are not limited to, oxygen ($O_2$), hydrogen cyanide (HCN), acetylene ($C_2H_2$), and BTEX (benzene, toluene, ethyl benzene, xylene).

"Catalyst inhibitor," "adsorbent inhibitor," and the like, as used herein, refer to one or more substances that decrease the rate of or prevent a chemical reaction. In particular embodiments, the catalyst inhibitors may include, but are not limited to, hydrogen sulfide ($H_2S$) and carbonyl sulfide (COS).

In certain instances, at least one constituent removed is produced, introduced, and/or concentrated by a fermentation step. One or more of these constituents may be present in a post-fermentation gaseous substrate. For example, sulfur, in the form of $H_2S$ may be produced, introduced, and/or concentrated by a fermentation step. In particular embodiments, hydrogen sulfide is introduced in the fermentation step. In various embodiments, the post-fermentation gaseous substrate comprises at least a portion of hydrogen sulfide. Hydrogen sulfide may be a catalyst inhibitor. As such, the hydrogen sulfide may be inhibiting to particular electrolysis modules. In order to pass a non-inhibiting post-fermentation gaseous substrate to the electrolyzer, at least a portion of the hydrogen sulfide, or other constituent present in the post-fermentation gaseous substrate, may need to be removed by one or more removal module. In another embodiment, acetone may be produced by a fermentation step, and charcoal may be used as a removal module.

The terms "treated gas" and "treated gas stream" refer to a gas stream that has been passed through at least one removal module and has had one or more constituent removed and/or converted. For example, a "$CO_2$-treated gas stream" refers to a $CO_2$-comprising gas that has passed through one or more removal module.

"Concentration module" and the like refer to technology capable of increasing the level of a particular component in a gas stream. In particular embodiments, the concentration module is a $CO_2$ concentration module, wherein the proportion of $CO_2$ in the gas stream leaving the $CO_2$ concentration module is higher relative to the proportion of $CO_2$ in the gas stream prior to being passed to the $CO_2$ concentration module. In some embodiments, a $CO_2$ concentration module uses deoxygenation technology to remove $O_2$ from a gas stream and thus increase the proportion of $CO_2$ in the gas stream. In some embodiments, a $CO_2$ concentration module uses pressure swing adsorption (PSA) technology to remove $H_2$ from a gas stream and thus increase the proportion of $CO_2$ in the gas stream. In certain instances, a fermentation process performs the function of a $CO_2$ concentration module. In some embodiments, a gas stream from a concentration module is passed to a carbon capture and sequestration (CCS) unit or an enhanced oil recovery (EOR) unit.

The terms "electrolysis module" and "electrolyzer" can be used interchangeably to refer to a unit that uses electricity to drive a non-spontaneous reaction. Electrolysis technologies are known in the art. Exemplary processes include alkaline water electrolysis, proton or anion exchange membrane (PEM, AEM) electrolysis, and solid oxide electrolysis (SOE) (Ursua et al., *Proceedings of the IEEE* 100(2):410-426, 2012; Jhong et al., *Current Opinion in Chemical Engineering* 2:191-199, 2013). The term "faradaic efficiency" is a value that references the number of electrons flowing through an electrolyzer and being transferred to a reduced product rather than to an unrelated process. SOE modules operate at elevated temperatures. Below the thermoneutral voltage of an electrolysis module, an electrolysis reaction is endothermic. Above the thermoneutral voltage of an electrolysis module, an electrolysis reaction is exothermic. In some embodiments, an electrolysis module is operated without added pressure. In some embodiments, an electrolysis module is operated at a pressure of 5-10 bar.

A "$CO_2$ electrolysis module" refers to a unit capable of splitting $CO_2$ into CO and $O_2$ and is defined by the following stoichiometric reaction: $2CO_2$+electricity→$2CO+O_2$. The use of different catalysts for $CO_2$ reduction impact the end product. Catalysts including, but not limited to, Au, Ag, Zn, Pd, and Ga catalysts, have been shown effective for the production of CO from $CO_2$. In some embodiments, the pressure of a gas stream leaving a $CO_2$ electrolysis module is approximately 5-7 barg.

"$H_2$ electrolysis module," "water electrolysis module," and "$H_2O$ electrolysis module" refer to a unit capable of splitting $H_2O$, in the form of steam, into $H_2$ and $O_2$ and is defined by the following stoichiometric reaction: $2H_2O$+electricity→$2H_2+O_2$. An $H_2O$ electrolysis module reduces protons to $H_2$ and oxidizes $O^{2-}$ to $O_2$. $H_2$ produced by electrolysis can be blended with a C1-comprising gaseous substrate as a means to supply additional feedstock and to improve substrate composition.

$H_2$ and $CO_2$ electrolysis modules have 2 gas outlets. One side of the electrolysis module, the anode, comprises $H_2$ or CO (and other gases such as unreacted water vapor or unreacted $CO_2$). The second side, the cathode, comprises $O_2$ (and potentially other gases). The composition of a feedstock being passed to an electrolysis process may determine the presence of various components in a CO stream. For instance, the presence of inert components, such as $CH_4$ and/or $N_2$, in a feedstock may result in one or more of those components being present in the CO-enriched stream. Additionally, in some electrolyzers, $O_2$ produced at the cathode crosses over to the anode side where CO is generated and/or CO crosses over to the anode side, leading to cross contamination of the desired gas products.

The term "separation module" is used to refer to a technology capable of dividing a substance into two or more components. For example, an "$O_2$ separation module" may be used to separate an $O_2$-comprising gaseous substrate into a stream comprising primarily $O_2$ (also referred to as an "$O_2$-enriched stream" or "$O_2$-rich gas") and a stream that does not primarily comprise $O_2$, comprises no $O_2$, or comprises only trace amounts of $O_2$ (also referred to as an "$O_2$-lean stream" or "$O_2$-depleted stream").

As used herein, the terms "enriched stream," "rich gas," "high purity gas," and the like refer to a gas stream having a greater proportion of a particular component following passage through a module, such as an electrolysis module, as compared to the proportion of the component in the input stream into the module. For example, a "CO-enriched stream" may be produced upon passage of a $CO_2$-comprising gaseous substrate through a $CO_2$ electrolysis module. An "$H_2$-enriched stream" may be produced upon passage of a water gaseous substrate through an $H_2$ electrolysis module. An "$O_2$-enriched stream" emerges automatically from the anode of a $CO_2$ or $H_2$ electrolysis module; an "$O_2$-enriched stream" may also be produced upon passage of an $O_2$-comprising gaseous substrate through an $O_2$ separation module. A "$CO_2$-enriched stream" may be produced upon passage of a $CO_2$-comprising gaseous substrate through a $CO_2$ concentration module.

As used herein, the terms "lean stream," "depleted gas," and the like refer to a gas stream having a lesser proportion of a particular component following passage through a module, such as a concentration module or a separation module, as compared to the proportion of the component in the input stream into the module. For example, an O$_2$-lean stream may be produced upon passage of an O$_2$-comprising gaseous substrate through an O$_2$ separation module. The O$_2$-lean stream may comprise unreacted CO$_2$ from a CO$_2$ electrolysis module. The O$_2$-lean stream may comprise trace amounts of O$_2$ or no O$_2$. A "CO$_2$-lean stream" may be produced upon passage of a CO$_2$-comprising gaseous substrate through a CO$_2$ concentration module. The CO$_2$-lean stream may comprise CO, H$_2$, and/or a constituent such as a microbe inhibitor or a catalyst inhibitor. The CO$_2$-lean stream may comprise trace amounts of CO$_2$ or no CO$_2$.

In particular embodiments, the invention provides an integrated process wherein the pressure of the gas stream is capable of being increased and/or decreased. The term "pressure module" refers to a technology capable of producing (i.e., increasing) or decreasing the pressure of a gas stream. The pressure of the gas may be increased and/or decreased through any suitable means, for example one or more compressor and/or valve. In certain instances, a gas stream may have a lower than optimum pressure, or the pressure of the gas stream may be higher than optimal, and thus, a valve may be included to reduce the pressure. A pressure module may be located before or after any module described herein. For example, a pressure module may be utilized prior to a removal module, prior to a concentration module, prior to an electrolysis module, and/or prior to a CO-consuming process.

A "pressurized gas stream" refers to a gaseous substrate that has passed through a pressure module. A "pressurized gas stream" may also be used to refer to a gas stream that meets the operating pressure requirements of a particular module.

The terms "post-CO-consuming process gaseous substrate," "post-CO-consuming process tail gas," "tail gas," and the like may be used interchangeably to refer to a gas that has passed through a CO-consuming process. The post-CO-consuming process gaseous substrate may comprise unreacted CO, unreacted H$_2$, and/or CO$_2$ produced (or not taken up in parallel) by the CO-consuming process. The post-CO-consuming process gaseous substrate may further be passed to one or more of a pressure module, a removal module, a CO$_2$ concentration module, and/or an electrolysis module. In some embodiments, a "post-CO-consuming process gaseous substrate" is a post-fermentation gaseous substrate.

The term "desired composition" is used to refer to the desired level and types of components in a substance, such as, for example, of a gas stream. More particularly, a gas is considered to have a "desired composition" if it contains a particular component (i.e., CO, H$_2$, and/or CO$_2$) and/or contains a particular component at a particular proportion and/or does not comprise a particular component (i.e., a contaminant harmful to the microorganisms) and/or does not comprise a particular component at a particular proportion. More than one component may be considered when determining whether a gas stream has a desired composition.

While it is not necessary for the substrate to comprise any H$_2$, the presence of H$_2$ should not be detrimental to product formation in accordance with methods of the invention. In particular embodiments, the presence of H$_2$ results in an improved overall efficiency of alcohol production. In one embodiment, the substrate comprises about 30% or less H$_2$ by volume, 20% or less H$_2$ by volume, about 15% or less H$_2$ by volume or about 10% or less H$_2$ by volume. In other embodiments, the substrate stream comprises low concentrations of H$_2$, for example, less than 5%, or less than 4%, or less than 3%, or less than 2%, or less than 1%, or is substantially H$_2$ free.

The substrate may also comprise some CO for example, such as about 1% to about 80% CO by volume, or 1% to about 30% CO by volume. In one embodiment, the substrate comprises less than or equal to about 20% CO by volume. In particular embodiments, the substrate comprises less than or equal to about 15% CO by volume, less than or equal to about 10% CO by volume, less than or equal to about 5% CO by volume or substantially no CO.

Substrate composition can be improved to provide a desired or optimum H$_2$:CO:CO$_2$ ratio. The desired H$_2$:CO:CO$_2$ ratio is dependent on the desired fermentation product of the fermentation process. For ethanol, the optimum H$_2$:CO:CO$_2$ ratio would be:

$$(x){:}(y){:}\left(\frac{x-2y}{3}\right),$$

where x>2y, in order to satisfy the stoichiometry for ethanol production:

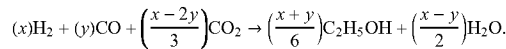

Operating the fermentation process in the presence of H$_2$ has the added benefit of reducing the amount of CO$_2$ produced by the fermentation process. For example, a gaseous substrate comprising minimal H$_2$ will typically produce ethanol and CO$_2$ by the following stoichiometry: 6 CO+3 H$_2$O→C$_2$H$_5$OH+4 CO$_2$. As the amount of H$_2$ utilized by the C1 fixing bacterium increase, the amount of CO$_2$ produced decreases, i.e., 2 CO+4 H$_2$→C$_2$H$_5$OH+H$_2$O.

When CO is the sole carbon and energy source for ethanol production, a portion of the carbon is lost to CO$_2$ as follows:

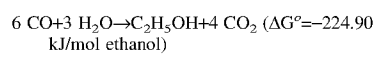

As the amount of H$_2$ available in the substrate increases, the amount of CO$_2$ produced decreases. At a stoichiometric ratio of 1:2 (CO/H$_2$), CO$_2$ production is completely avoided.

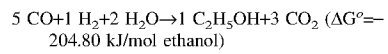

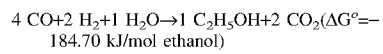

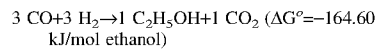

The composition of the substrate may have a significant impact on the efficiency and/or cost of the reaction. For example, the presence of O$_2$ may reduce the efficiency of an anaerobic fermentation process. Depending on the composition of the substrate, it may be desirable to treat, scrub, or filter the substrate to remove any undesired impurities, such as toxins, undesired components, or dust particles, and/or increase the concentration of desirable components. Furthermore, carbon capture can be increased by recycling CO$_2$ produced by a CO-consuming process back to a CO$_2$ electrolysis module, thereby improving yield of the CO-consuming process. CO$_2$ produced by the CO-consuming process may be treated prior to passage through the CO$_2$ electrolysis module.

In some embodiments, a CO-consuming process is performed in a bioreactor. The term "bioreactor" includes a fermentation device consisting of one or more vessels and/or towers or piping arrangements, which includes the Continuous Stirred Tank Reactor (CSTR), Immobilized Cell Reactor (ICR), Trickle Bed Reactor (TBR), Bubble Column, Gas Lift Fermenter, Static Mixer, a circulated loop reactor, a membrane reactor, such as a Hollow Fibre Membrane Bioreactor (HFM BR) or other vessel or other device suitable for gas-liquid contact. The reactor is preferably adapted to receive a gaseous substrate comprising CO, $CO_2$, $H_2$, or mixtures thereof. The reactor may comprise multiple reactors (stages), either in parallel or in series. For example, the reactor may comprise a first growth reactor in which the bacteria are cultured and a second fermentation reactor, to which fermentation broth from the growth reactor may be fed and in which most of the fermentation products may be produced.

Operating a bioreactor at elevated pressures allows for an increased rate of gas mass transfer from the gas phase to the liquid phase. Accordingly, it is generally preferable to perform the culture/fermentation at pressures higher than atmospheric pressure. Also, since a given gas conversion rate is, in part, a function of the substrate retention time and retention time dictates the required volume of a bioreactor, the use of pressurized systems can greatly reduce the volume of the bioreactor required and, consequently, the capital cost of the culture/fermentation equipment. This, in turn, means that the retention time, defined as the liquid volume in the bioreactor divided by the input gas flow rate, can be reduced when bioreactors are maintained at elevated pressure rather than atmospheric pressure. The optimum reaction conditions will depend partly on the particular microorganism used. However, in general, it is preferable to operate the fermentation at a pressure higher than atmospheric pressure. Also, since a given gas conversion rate is in part a function of substrate retention time and achieving a desired retention time in turn dictates the required volume of a bioreactor, the use of pressurized systems can greatly reduce the volume of the bioreactor required, and consequently the capital cost of the fermentation equipment.

Unless the context requires otherwise, the phrases "fermenting," "fermentation process," "fermentation reaction" and the like, as used herein, are intended to encompass both the growth phase and product biosynthesis phase of the gaseous substrate. In certain embodiments, the fermentation is performed in the absence of carbohydrate substrates, such as sugar, starch, lignin, cellulose, or hemicellulose.

A culture is generally maintained in an aqueous culture medium that contains nutrients, vitamins, and/or minerals sufficient to permit growth of a microorganism. "Nutrient media," "nutrient medium," and "culture medium" are used to describe bacterial growth media. Preferably, the aqueous culture medium is an anaerobic microbial growth medium, such as a minimal anaerobic microbial growth medium. Suitable media are well known in the art. The term "nutrient" includes any substance that may be utilised in a metabolic pathway of a microorganism. Exemplary nutrients include potassium, B vitamins, trace metals, and amino acids.

The terms "fermentation broth" and "broth" are intended to encompass the mixture of components including nutrient media and a culture or one or more microorganisms. It should be noted that the term microorganism and the term bacteria are used interchangeably herein.

A microorganism of the invention may be cultured with a gas stream to produce one or more products. For instance, a microorganism of the invention may produce or may be engineered to produce ethanol (WO 2007/117157), acetate (WO 2007/117157), butanol (WO 2008/115080 and WO 2012/053905), butyrate (WO 2008/115080), 2,3-butanediol (WO 2009/151342 and WO 2016/094334), lactate (WO 2011/112103), butene (WO 2012/024522), butadiene (WO 2012/024522), methyl ethyl ketone (2-butanone) (WO 2012/024522 and WO 2013/185123), ethylene (WO 2012/026833), acetone (WO 2012/115527), isopropanol (WO 2012/115527), lipids (WO 2013/036147), 3-hydroxypropionate (3-HP) (WO 2013/180581), terpenes, including isoprene (WO 2013/180584), fatty acids (WO 2013/191567), 2-butanol (WO 2013/185123), 1,2-propanediol (WO 2014/036152), 1-propanol (WO 2014/0369152), chorismate-derived products (WO 2016/191625), 3-hydroxybutyrate (WO 2017/066498), and 1,3-butanediol (WO 2017/0066498). In addition to one or more target products, a microorganism of the invention may also produce ethanol, acetate, and/or 2,3-butanediol. In certain embodiments, microbial biomass itself may be considered a product. These products may be further converted to produce at least one component of diesel, jet fuel, and/or gasoline. Additionally, the microbial biomass may be further processed to produce a single cell protein (SCP).

A "microorganism" is a microscopic organism, especially a bacterium, archea, virus, or fungus. A microorganism of the invention is typically a bacterium. As used herein, recitation of "microorganism" should be taken to encompass "bacterium."

A "parental microorganism" is a microorganism used to generate a microorganism of the invention. The parental microorganism may be a naturally-occurring microorganism (i.e., a wild-type microorganism) or a microorganism that has been previously modified (i.e., a mutant or recombinant microorganism). A microorganism of the invention may be modified to express or overexpress one or more enzymes that were not expressed or overexpressed in the parental microorganism. Similarly, a microorganism of the invention may be modified to comprise one or more genes that were not contained by the parental microorganism. A microorganism of the invention may also be modified to not express or to express lower amounts of one or more enzymes that were expressed in the parental microorganism. In one embodiment, the parental microorganism is *Clostridium autoethanogenum*, *Clostridium ljungdahlii*, or *Clostridium ragsdalei*. In a preferred embodiment, the parental microorganism is *Clostridium autoethanogenum* LZ1561, which was deposited on Jun. 7, 2010 with Deutsche Sammlung von Mikroorganismen and Zellkulturen GmbH (DSMZ) located at Inhoffenstraβ 7B, D-38124 Braunschwieg, Germany on Jun. 7, 2010 under the terms of the Budapest Treaty and accorded accession number DSM23693. This strain is described in International Patent Application No. PCT/NZ2011/000144, which published as WO 2012/015317.

The term "derived from" indicates that a nucleic acid, protein, or microorganism is modified or adapted from a different (i.e., a parental or wild-type) nucleic acid, protein, or microorganism, so as to produce a new nucleic acid, protein, or microorganism. Such modifications or adaptations typically include insertion, deletion, mutation, or substitution of nucleic acids or genes. Generally, a microorganism of the invention is derived from a parental microorganism. In one embodiment, a microorganism of the invention is derived from *Clostridium autoethanogenum*, *Clostridium ljungdahlii*, or *Clostridium ragsdalei*. In a preferred embodiment, a microorganism of the invention is derived from *Clostridium autoethanogenum* LZ1561, which is deposited under DSMZ accession number DSM23693.

A microorganism of the invention may be further classified based on functional characteristics. For example, the microorganism of the invention may be or may be derived from a C1-fixing microorganism, an anaerobe, an acetogen, an ethanologen, a carboxydotroph, and/or a methanotroph.

"Wood-Ljungdahl" refers to the Wood-Ljungdahl pathway of carbon fixation as described, i.e., by Ragsdale, *Biochim Biophys Acta,* 1784: 1873-1898, 2008. "Wood-Ljungdahl microorganisms" refers, predictably, to microorganisms comprising the Wood-Ljungdahl pathway. Generally, a microorganism of the invention contains a native Wood-Ljungdahl pathway. Herein, a Wood-Ljungdahl pathway may be a native, unmodified Wood-Ljungdahl pathway or it may be a Wood-Ljungdahl pathway with some degree of genetic modification (i.e., overexpression, heterologous expression, knockout, etc.) so long as it still functions to convert CO, $CO_2$, and/or $H_2$ to acetyl-CoA.

An "anaerobe" is a microorganism that does not require $O_2$ for growth. An anaerobe may react negatively or even die if $O_2$ is present above a certain threshold. However, some C1-fixing, anaerobic, autotrophic, and non-methanotrophic. Typically, a microorganism of the invention is an acetogen.

An "ethanologen" is a microorganism that produces or is capable of producing ethanol. Typically, a microorganism of the invention is an ethanologen.

An "autotroph" is a microorganism capable of growing in the absence of organic carbon. Instead, autotrophs use inorganic carbon sources, such as CO and/or $CO_2$. Typically, a microorganism of the invention is an autotroph.

A "carboxydotroph" is a microorganism capable of utilizing CO as a sole source of carbon and energy. Typically, a microorganism of the invention is a carboxydotroph.

A "methanotroph" is a microorganism capable of utilizing methane as a sole source of carbon and energy. In certain embodiments, a microorganism of the invention is a methanotroph or is derived from a methanotroph. In other embodiments, a microorganism of the invention is not a methanotroph or is not derived from a methanotroph.

Table 1 provides a representative list of microorganisms and identifies their functional characteristics.

TABLE 1

| | Wood-Ljungdahl | C1-fixing | Anaerobe | Acetogen | Ethanologen | Autotroph | Carboxydotroph |
|---|---|---|---|---|---|---|---|
| *Acetobacterium woodii* | + | + | + | + | +/− [1] | + | − |
| *Alkalibaculum bacchii* | + | + | + | + | + | + | + |
| *Blautia producta* | + | + | + | + | − | + | + |
| *Butyribacterium methylotrophicum* | + | + | + | + | + | + | + |
| *Clostridium aceticum* | + | + | + | + | − | + | + |
| *Clostridium autoethanogenum* | + | + | + | + | + | + | + |
| *Clostridium carboxidivorans* | + | + | + | + | + | + | + |
| *Clostridium coskatii* | + | + | + | + | + | + | + |
| *Clostridium drakei* | + | + | + | + | − | + | + |
| *Clostridium formicoaceticum* | + | + | + | + | − | + | + |
| *Clostridium ljungdahlii* | + | + | + | + | + | + | + |
| *Clostridium magnum* | + | + | + | + | − | + | +/− [2] |
| *Clostridium ragsdalei* | + | + | + | + | + | + | + |
| *Clostridium scatologenes* | + | + | + | + | − | + | + |
| *Eubacterium limosum* | + | + | + | + | − | + | + |
| *Moorella thermautotrophica* | + | + | + | + | + | + | + |
| *Moorella thermoacetica* (formerly *Clostridium thermoacelicum*) | + | + | + | + | − [3] | + | + |
| *Oxobacter pfennigii* | + | + | + | + | − | + | + |
| *Sporomusa ovata* | + | + | + | + | − | + | +/− [4] |
| *Sporomusa silvacetica* | + | + | + | + | − | + | +/− [5] |
| *Sporomusa sphaeroides* | + | + | + | + | − | + | +/− [6] |
| *Thermoanaerobacter kiuvi* | + | + | + | + | − | + | − |

[1] *Acetobacterium woodii* can produce ethanol from fructose, but not from gas.
[2] It has not been investigated whether *Clostridium magnum* can grow on CO.
[3] One strain of *Moorella thermoacetica*, *Moorella* sp. HUC22-1, has been reported to produce ethanol from gas.
[4] It has not been investigated whether *Sporomusa ovata* can grow on CO.
[5] It has not been investigated whether *Sporomusa silvacetica* can grow on CO.
[6] It has not been investigated whether *Sporomusa sphaeroides* can grow on CO.

anaerobes are capable of tolerating low levels of $O_2$ (i.e., 0.000001-5% $O_2$). Typically, a microorganism of the invention is an anaerobe.

"Acetogens" are obligately anaerobic bacteria that use the Wood-Ljungdahl pathway as their main mechanism for energy conservation and for synthesis of acetyl-CoA and acetyl-CoA-derived products, such as acetate (Ragsdale, *Biochim Biophys Acta,* 1784: 1873-1898, 2008). In particular, acetogens use the Wood-Ljungdahl pathway as a (1) mechanism for the reductive synthesis of acetyl-CoA from $CO_2$, (2) terminal electron-accepting, energy conserving process, (3) mechanism for the fixation (assimilation) of $CO_2$ in the synthesis of cell carbon (Drake, Acetogenic Prokaryotes, In: The Prokaryotes, 3$^{rd}$ edition, p. 354, New York, N.Y., 2006). All naturally occurring acetogens are A "native product" is a product produced by a genetically unmodified microorganism. For example, ethanol, acetate, and 2,3-butanediol are native products of *Clostridium autoethanogenum, Clostridium ljungdahlii,* and *Clostridium ragsdalei.* A "non-native product" is a product that is produced by a genetically modified microorganism but is not produced by a genetically unmodified microorganism from which the genetically modified microorganism is derived.

"Selectivity" refers to the ratio of the production of a target product to the production of all fermentation products produced by a microorganism. A microorganism of the invention may be engineered to produce products at a certain selectivity or at a minimum selectivity. In one embodiment, a target product account for at least about 5%, 10%, 15%, 20%, 30%, 50%, or 75% of all fermentation products produced by a microorganism of the invention. In one embodiment, the target product accounts for at least 10% of all fermentation products produced by a microorganism of the invention, such that a microorganism of the invention has a selectivity for the target product of at least 10%. In another embodiment, the target product accounts for at least 30% of all fermentation products produced by a microorganism of the invention, such that a microorganism of the invention has a selectivity for the target product of at least 30%.

A culture/fermentation should desirably be carried out under appropriate conditions for production of the target product. Typically, the culture/fermentation is performed under anaerobic conditions. Reaction conditions to consider include pressure (or partial pressure), temperature, gas flow rate, liquid flow rate, media pH, media redox potential, agitation rate (if using a continuous stirred tank reactor), inoculum level, maximum gas substrate concentrations to ensure that gas in the liquid phase does not become limiting, and maximum product concentrations to avoid product inhibition. In particular, the rate of introduction of the substrate may be controlled to ensure that the concentration of gas in the liquid phase does not become limiting, since products may be consumed by the culture under gas-limited conditions.

Target products may be separated or purified from a fermentation broth using any method or combination of methods known in the art, including, for example, fractional distillation, evaporation, pervaporation, gas stripping, phase separation, and extractive fermentation, including for example, liquid-liquid extraction. In certain embodiments, target products are recovered from the fermentation broth by continuously removing a portion of the broth from the bioreactor, separating microbial cells from the broth (conveniently by filtration), and recovering one or more target products from the broth. Alcohols and/or acetone may be recovered, for example, by distillation. Acids may be recovered, for example, by adsorption on activated charcoal. Separated microbial cells are preferably returned to the bioreactor. The cell-free permeate remaining after target products have been removed is also preferably returned to the bioreactor. Additional nutrients (such as B vitamins) may be added to the cell-free permeate to replenish the medium before it is returned to the bioreactor.

FIG. 1A shows a process for integration of an industrial process 110, one or more removal module 120, a $CO_2$ electrolysis process 130, an optional $H_2$ electrolysis process 160, and a CO-consuming process 140. $CO_2$-comprising gas from an industrial process 110 is fed via a conduit 112 to one or more removal module 120 to remove and/or convert one or more constituent 128. The treated gas from the one or more removal module 120 is then fed via a conduit 122 to a $CO_2$ electrolysis module 130 for conversion of at least a portion of the gas stream. In some embodiments, $CO_2$-comprising gas from the industrial process 110 is directly fed via a conduit 114 to the $CO_2$ electrolysis module 130 for conversion of at least a portion of the gas stream; in this embodiment, a constituent such as sulfur may be removed prior to passage through an industrial process. Optionally, at least a portion of $O_2$ may be fed from the $CO_2$ electrolysis module 130 to the industrial process 110 via a conduit 136. At least a portion of the converted gas stream is passed, via a conduit 132, from the $CO_2$ electrolysis module 130 to a CO-consuming process 140. In some embodiments, a water substrate is fed via a conduit 162 to an $H_2$ electrolysis module 160 for conversion of at least a portion of the water substrate, and an $H_2$-enriched stream is passed via a conduit 164 to the CO-consuming process 140. Optionally, at least a portion of $O_2$ may be fed from the $H_2$ electrolysis module 160 to the industrial process 110 via a conduit 166. The CO-consuming process 140 produces at least one product 146 and a post-CO-consuming process gaseous substrate.

The CO-consuming process 140 of FIG. 1A may be a gas fermentation process and may occur in an inoculator and/or one or more bioreactors. For example, the CO-consuming process 140 may be a gas fermentation process in a bioreactor comprising a culture of at least one C1-fixing microorganism. In embodiments wherein the CO-consuming process 140 is a gas fermentation process, a culture may be fermented to produce one or more fermentation products 146 and a post-fermentation gaseous substrate (CO-consuming process gaseous substrate).

In some embodiments, the CO-consuming process 140 of FIG. 1A comprises a $CO_2$-producing reaction step. In embodiments wherein a post-CO-consuming process gaseous substrate comprises $CO_2$, at least a portion of the post-CO-consuming process gaseous substrate is passed via a conduit 142 to one or more removal module 150 to remove and/or convert one or more constituent 158. A treated gas stream comprising $CO_2$ is then passed via a conduit 152 to a $CO_2$ electrolysis module 130 for conversion of at least a portion of the gas stream. In particular embodiments, the post-CO-consuming process gaseous substrate is passed via a conduit 142 to the same one or more removal module 120 that receives $CO_2$-comprising gas from the industrial process 110. In various embodiments, the post-CO-consuming process gaseous substrate may be passed to the one or more removal module 120 that receives the $CO_2$-comprising gas from the industrial process 110 and the one or more removal module 150. This process of treating and electrolyzing the post-CO-consuming process gaseous substrate has been found to increase carbon capture efficiency.

In particular embodiments, at least one constituent removed by the removal module 150 of FIG. 1A is produced, introduced, and/or concentrated by the CO-consuming process 140, such as a gas fermentation process. In various embodiments, the one or more constituent produced, introduced, and/or concentrated by the fermentation step comprises sulfur. In certain instances, sulfur, such as hydrogen sulfide, is introduced to the CO-consuming process 140. This sulfur was found to reduce the efficiency of the $CO_2$ electrolysis module 130. The removal module 150 was found to be successful at reducing the amount of sulfur in the post-CO-consuming process gaseous substrate prior to the post-CO-consuming process gaseous substrate being passed to the $CO_2$ electrolysis module 130. The use of the removal module 150 prior to the $CO_2$ electrolysis module 130 was found to increase the efficiency of the $CO_2$ electrolysis module 130.

The inventors have identified that the $O_2$ by-product of $CO_2$ and $H_2$ electrolysis processes can provide additional benefits for the C1-generating industrial process. While fermentation processes of the current invention are anaerobic processes, the inventors have identified that the $O_2$ by-product of the CO production process, such as $O_2$ passed through conduit 136 in of FIG. 1A, can be used in a C1-generating industrial process. The high-purity $O_2$ by-product of the $CO_2$ electrolysis process can be integrated with the industrial process and beneficially offset costs, and in some cases, have synergy that further reduces costs for both the industrial process as well as the subsequent gas fermentation.

Typically, the industrial processes described herein derive the required $O_2$ by air separation. Production of $O_2$ by air separation is an energy intensive process which involves cryogenically separating $O_2$ from $N_2$ to achieve the highest purity. Production of $O_2$ by $CO_2$ and/or $H_2$ electrolysis, and displacing $O_2$ produced by air separation, could offset up to 5% of the electricity costs in an industrial process.

Several C1-generating industrial processes involving partial oxidation reactions require an $O_2$ input. Exemplary industrial processes include Basic Oxygen Furnace (BOF) reactions, COREX or FINEX steel making processes, Blast Furnace (BF) processes, ferroalloy production processes, titanium dioxide production processes, and gasification processes. Gasification processes include, but are not limited to, municipal solid waste gasification, biomass gasification, pet coke gasification, and coal gasification. In one or more of these industrial processes, $O_2$ from the $CO_2$ electrolysis process may be used to off-set or completely replace the $O_2$ typically supplied through air separation.

Figure 1B:
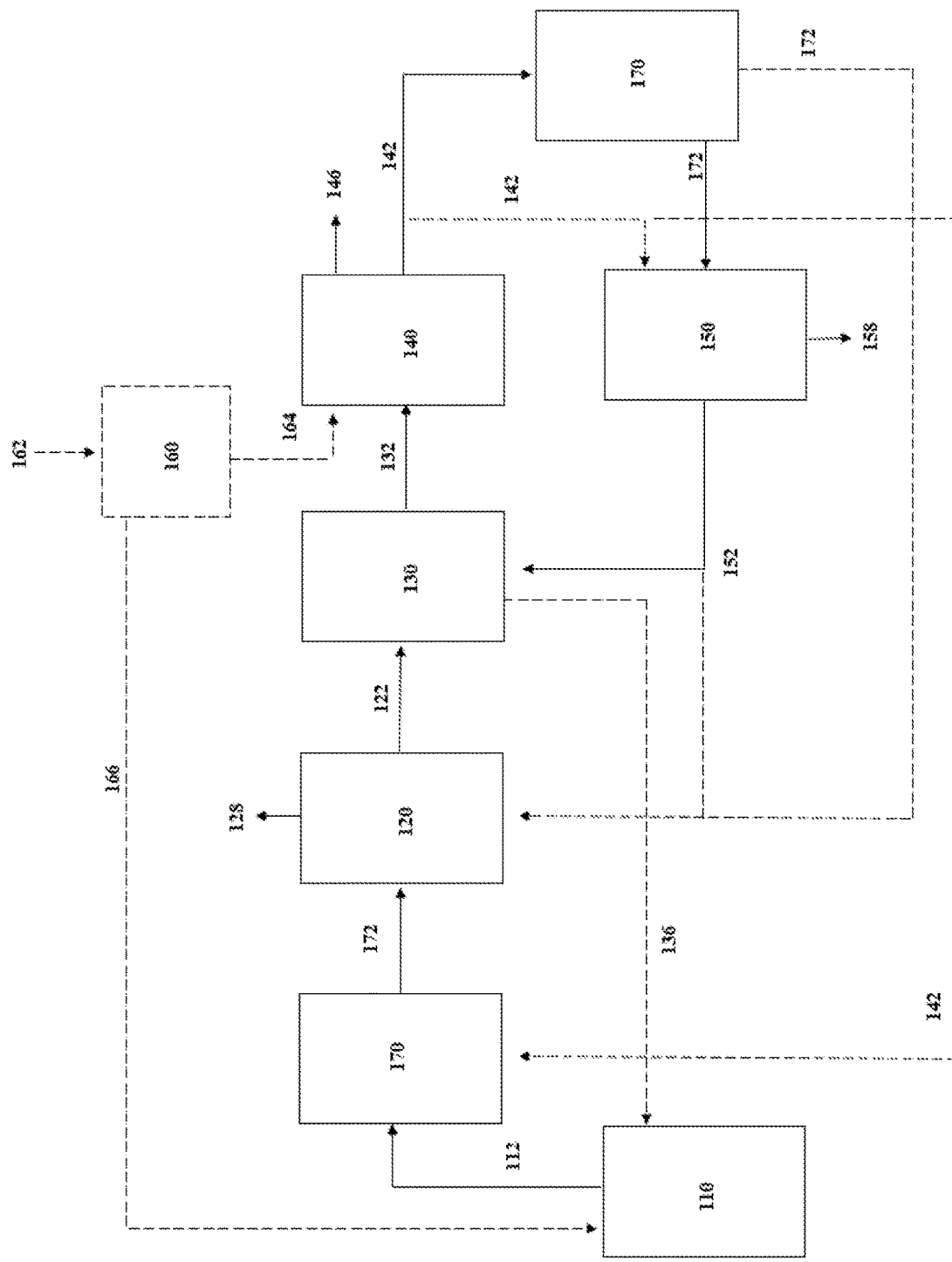
Figure 1C:
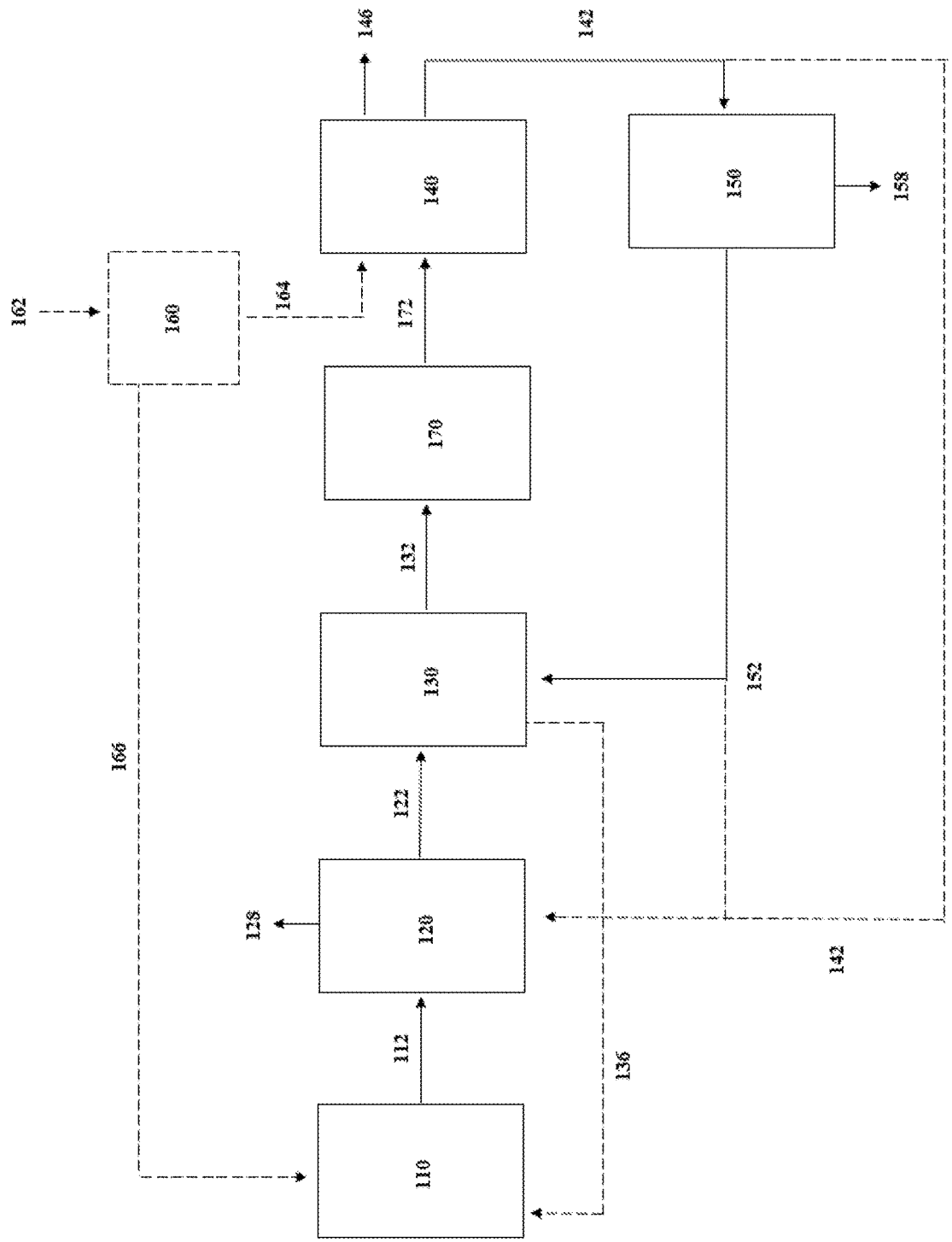

As shown in FIGS. 1B and 1C, a process for integration of an industrial process, one or more removal module, a $CO_2$ electrolysis process, an optional $H_2$ electrolysis process, and a CO-consuming process may further comprise integration of one or more pressure module 170. For example, as shown in FIG. 1B, at least a portion of $CO_2$-comprising gas from an industrial process 110 is fed via a conduit 112 to a pressure module 170 to produce a pressurized $CO_2$-comprising gas stream. At least a portion of the pressurized $CO_2$-comprising gas stream is then passed via a conduit 172 to a removal module 120. At least a portion of post-CO-consuming process gaseous substrate may also be passed via conduit 142 to a pressure module 170 to produce a pressurized tail gas. At least a portion of the pressurized tail gas is then passed via a conduit 172 to a removal module 150 and/or a removal module 120. As shown in FIG. 1C, at least a portion of a converted gas stream is passed, via a conduit 132, from a $CO_2$ electrolysis module 130 to a pressure module 170 to produce a pressurized CO-comprising gas stream, which is passed via a conduit 172 to a CO-consuming process 140.

Figure 2:
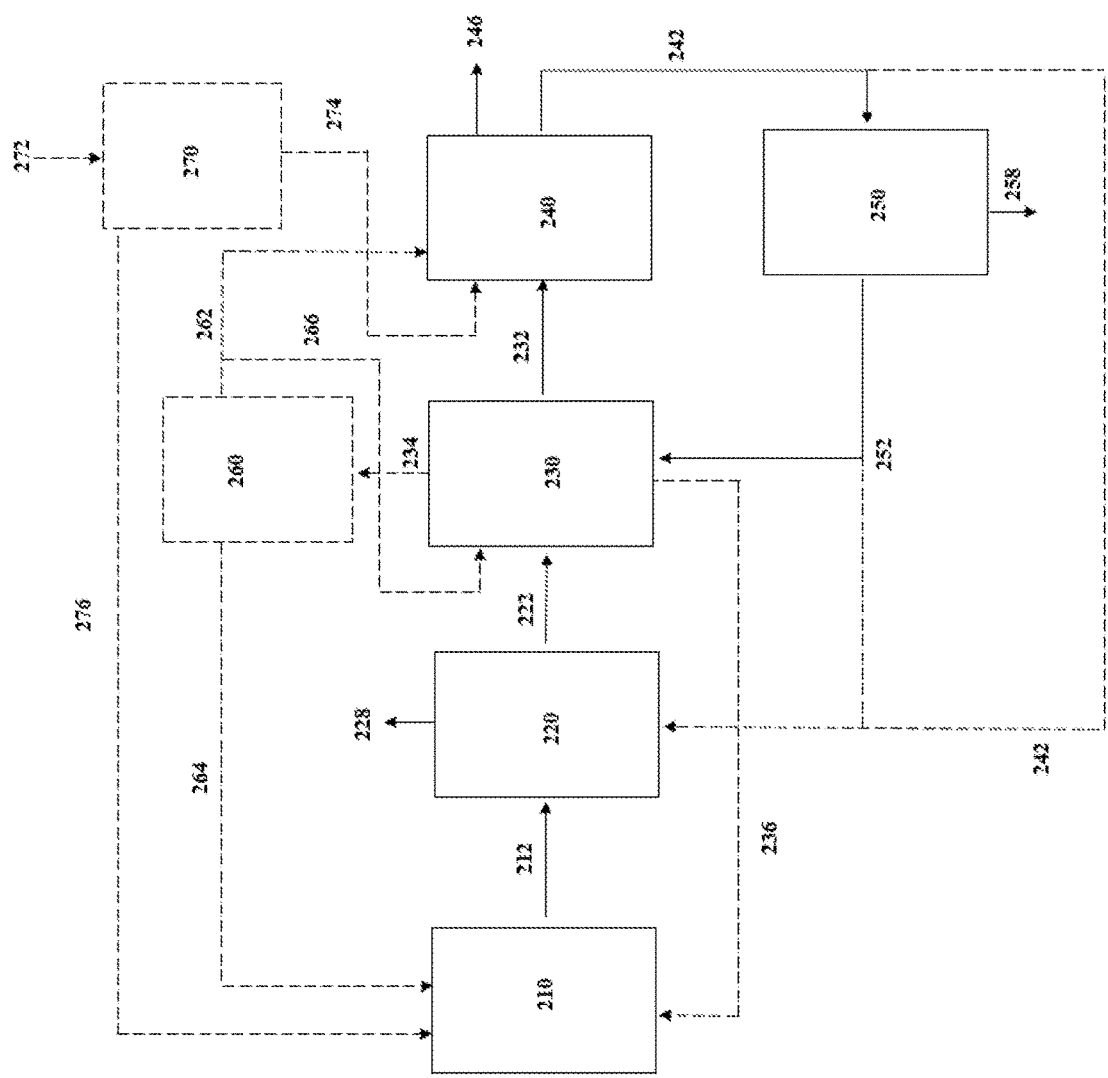
FIG. 2 shows a process integration scheme depicting integration of a removal module, a $CO_2$ electrolysis module, an optional $O_2$ separation module, and an optional $H_2$ electrolysis module with a CO-consuming process.

FIG. 2 shows a process for integration of an industrial process 210, a removal module 220, a $CO_2$ electrolysis module 230, an optional $H_2$ electrolysis process 270, a CO-consuming process 240, and an optional $O_2$ separation module 260. $CO_2$-comprising gas from an industrial process 210 is fed via a conduit 212 to one or more removal module 220 to remove and/or convert one or more constituent 228. The treated gas from the one or more removal module 220 is then fed via a conduit 222 to a $CO_2$ electrolysis module 230 for conversion of at least a portion of the gas stream. Optionally, at least a portion of $O_2$ may be fed from the $CO_2$ electrolysis module 230 to the industrial process 210 via a conduit 236. At least a portion of the converted gas stream is passed from the $CO_2$ electrolysis module 230 to the CO-consuming process 240 via a conduit 232 to produce a product 246 and a post-CO-consuming process gaseous substrate. In some embodiments, a water substrate is fed via a conduit 272 to an $H_2$ electrolysis module 270 for conversion of at least a portion of the water substrate, and an $H_2$-enriched stream is passed via a conduit 274 to the CO-consuming process 240. Optionally, at least a portion of $O_2$ may be fed from the $H_2$ electrolysis module 270 to the industrial process 210 via a conduit 276.

In particular embodiments, the process includes an $O_2$ separation module 260 following the $CO_2$ electrolysis module 230 to separate at least a portion of $O_2$ from the gas stream. In embodiments utilizing an $O_2$ separation module 260 after the $CO_2$ electrolysis module 230, at least a portion of the gas stream is fed from the $CO_2$ electrolysis module 230 to the $O_2$ separation module 260, via a conduit 234. In embodiments incorporating an $O_2$ separation module 260, at least a portion of $O_2$ separated from the gas stream from the $O_2$ separation module 260 ($O_2$-enriched stream) may be fed to the industrial process 210 via a conduit 264. In embodiments utilizing an $O_2$ separation module 260 after the $CO_2$ electrolysis module 230, at least a portion of the $O_2$-lean stream is fed from the $O_2$ separation module 260 to the CO-consuming process 240 via a conduit 262. In some embodiments utilizing an $O_2$ separation module 260 after the $CO_2$ electrolysis module 230, at least a portion of the $O_2$-lean stream is fed from the $O_2$ separation module 260 back to the $CO_2$ electrolysis module 230 via a conduit 266. In embodiments not utilizing an $O_2$ separation module 260, a portion of the gas stream may be fed from the $CO_2$ electrolysis module 230 to the industrial process 210 via a conduit 236.

In some embodiments, the CO-consuming process 240 of FIG. 2 comprises a $CO_2$-producing reaction step. In embodiments wherein the post-CO-consuming process gaseous substrate comprises $CO_2$, at least a portion of the post-CO-consuming process gaseous substrate is passed via a conduit 242 to one or more removal module 250 to remove and/or convert one or more constituent 258. A treated gas stream is then passed via a conduit 252 to a $CO_2$ electrolysis module 230 for conversion of at least a portion of the gas stream. In particular embodiments, the post-CO-consuming process gaseous substrate is passed via a conduit 242 to the same one or more removal module 220 that receives the $CO_2$-comprising gas from the industrial process 210. In various embodiments, the post-CO-consuming process gaseous substrate may be passed to the one or more removal module 220 that receives the $CO_2$-comprising gas from the industrial process 210 and the one or more removal module 250.

The CO-consuming process 240 of FIG. 2 may be a gas fermentation process and may occur in an inoculator and/or one or more bioreactors. For example, the CO-consuming process 240 may be a gas fermentation process in a bioreactor comprising a culture of at least one C1-fixing microorganism. In embodiments wherein the CO-consuming process 240 is a gas fermentation process, a culture may be fermented to produce one or more fermentation products 246 and a post-fermentation gaseous substrate (post-CO-consuming process gaseous substrate).

The provision of a high purity $CO_2$ stream ($CO_2$-rich stream) to a $CO_2$ electrolysis process has been found to increase the (carbon capture) efficiency of a CO-consuming process. To increase the concentration of $CO_2$ in a stream, one or more $CO_2$ concentration module may be incorporated in the process. Preferably, the post electrolysis stream has a concentration of CO between 20-90%.

Figure 3:
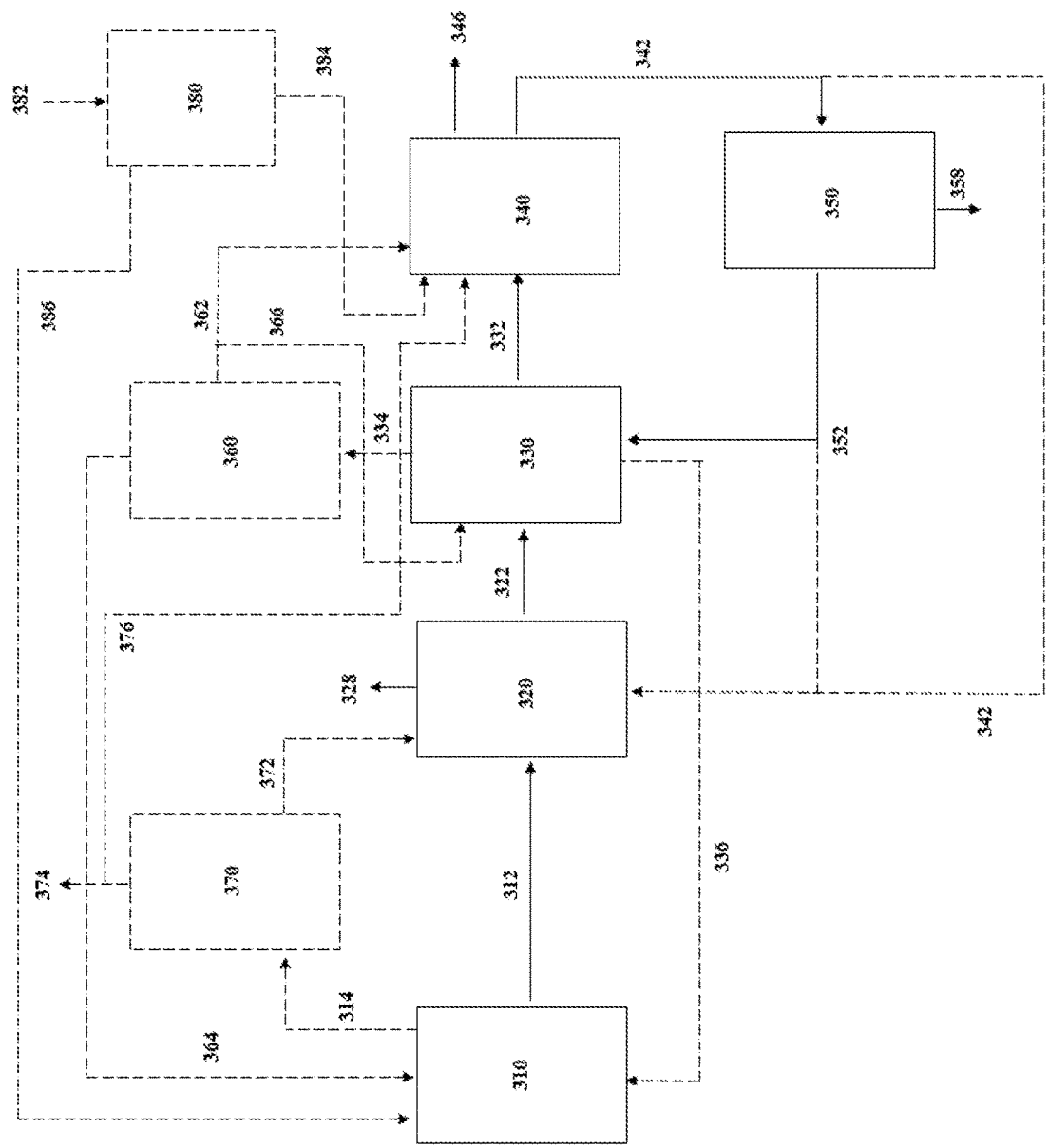
FIG. 3 shows a process integration scheme depicting integration of an optional $CO_2$ concentration module prior to a removal module, a $CO_2$ electrolysis module, an optional $H_2$ electrolysis module, and an optional $O_2$ separation module with a CO-consuming process.

FIG. 3 shows a process for integration of an industrial process 310 with an optional $CO_2$ concentration module 370, a removal module 320, a $CO_2$ electrolysis module 330, an optional $H_2$ electrolysis module 380, a CO-consuming process 340, and an optional $O_2$ separation module 360, in accordance with one aspect of the invention. In embodiments not including the $CO_2$ concentration module 370, $CO_2$-comprising gas from the industrial process 310 is fed via a conduit 312 to a removal module 320. In embodiments including the $CO_2$ concentration module 370, $CO_2$-comprising gas from the industrial process 310 is fed via a conduit 314 to a $CO_2$ concentration module 370 in order to increase the concentration of $CO_2$ in the gas stream and to remove one or more constituent 374. The $CO_2$-concentrated gas stream is then fed via a conduit 372 to one or more removal module 320 to remove and/or convert one or more constituent 328. The treated gas from the one or more removal module 320 is then fed via a conduit 322 to a CO$_2$ electrolysis module 330 for conversion of at least a portion of the gas stream. At least a portion of the converted gas stream is passed from the CO$_2$ electrolysis module 330 to the CO-consuming process 340 via a conduit 332. In some embodiments, the constituent 374 is CO and/or H$_2$, which is passed via conduit 376 to the CO-consuming process 340. In some embodiments, a water substrate is fed via a conduit 382 to an H$_2$ electrolysis module 380 for conversion of at least a portion of the water substrate, and an H$_2$-enriched stream is passed via a conduit 384 to the CO-consuming process 340. Optionally, at least a portion of O$_2$ may be fed from the H$_2$ electrolysis module 380 to the industrial process 310 via a conduit 386.

At least a portion of the gas stream from the CO$_2$ electrolysis module 330 may be passed to the industrial process 310 via a conduit 336. In particular embodiments, the process includes an O$_2$ separation module 360 following the CO$_2$ electrolysis module 330, where the gas stream is passed from the CO$_2$ electrolysis module 330 to the O$_2$ separation module 360 via a conduit 334 to separate at least a portion of O$_2$ from the gas stream. In embodiments utilizing an O$_2$ separation module 360 after the CO$_2$ electrolysis module 330, at least a portion of the removed O$_2$ (O$_2$-enriched stream) is fed from the O$_2$ separation module 360 to the industrial process 310 via a conduit 364. In embodiments utilizing an O$_2$ separation module 360 after the CO$_2$ electrolysis module 330, at least a portion of the O$_2$-lean stream is fed from the O$_2$ separation module 360 to the CO-consuming process 340 via a conduit 362. In some embodiments utilizing an O$_2$ separation module 360 after the CO$_2$ electrolysis module 330, at least a portion of the O$_2$-lean stream is fed from the O$_2$ separation module 260 back to the CO$_2$ electrolysis module 330 via a conduit 366. In embodiments not utilizing an O$_2$ separation module 360, a portion of the gas stream may be fed from the CO$_2$ electrolysis module 330 to the industrial process 310 via a conduit 336.

The process of concentrating the CO$_2$ in the gas stream prior to the one or more removal modules 320 has been found to decrease undesired gases, thereby increasing the efficiency of a CO-consuming process, such as a fermentation process. The amount of O$_2$ generated at the anode side of an electrolysis module is 50% the amount of CO$_2$ produced at the cathode of the electrolysis module. The produced O$_2$ can be used to increase the efficiency of the industrial process 310, wherein at least a portion of the gas stream following electrolysis is passed to the industrial process 310.

In some embodiments, the CO-consuming process 340 of FIG. 3 comprises a CO$_2$-producing reaction step. In embodiments wherein the post-CO-consuming process gaseous substrate comprises CO$_2$, the post-CO-consuming process gaseous substrate is passed via a conduit 342 to one or more removal module 350 to remove and/or convert one or more constituent 358. The treated gas stream is then passed via a conduit 352 to a CO$_2$ electrolysis module 330 for conversion of at least a portion of the gas stream. In particular embodiments, the post-CO-consuming process gaseous substrate is passed via a conduit 342 to the one or more removal module 320 that receives the CO$_2$-comprising gas from the industrial process 310. In various embodiments, the post-CO-consuming process gaseous substrate may be passed to the one or more removal module 320 that receives the CO$_2$-comprising gas from the industrial process 310 and the one or more removal module 350.

The CO-consuming process 340 of FIG. 3 may be a gas fermentation process and may occur in an inoculator and/or one or more bioreactors. For example, the CO-consuming process may be a gas fermentation process in a bioreactor comprising a culture of at least one C1-fixing microorganism. In the CO-consuming process 340, the culture is fermented to produce one or more fermentation products 346 and a post-CO-consuming process gaseous substrate.

Figure 4:
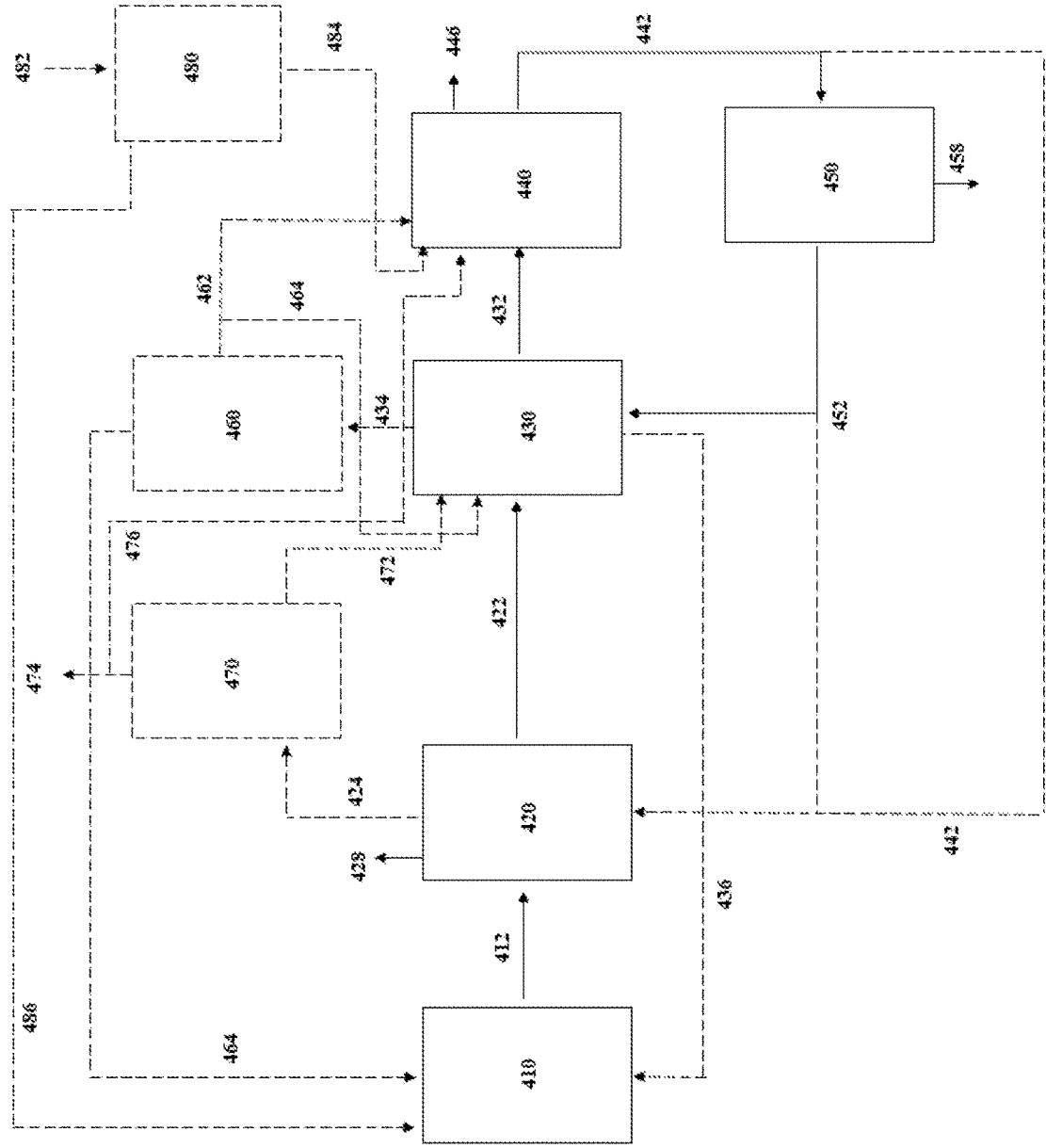
FIG. 4 shows a process integration scheme depicting integration of an optional $CO_2$ concentration module following a removal module, a $CO_2$ electrolysis module, an optional $H_2$ electrolysis module, and an optional $O_2$ separation module with a CO-consuming process.

In particular embodiments, a CO$_2$ concentration module may be placed after a removal module. FIG. 4 shows a process for integration of an industrial process 410 with a removal module 420, an optional CO$_2$ concentration module 470, a CO$_2$ electrolysis module 430, an optional H$_2$ electrolysis module 480, a CO-consuming process 440, and an optional O$_2$ separation module 460, in accordance with one aspect of the invention. In embodiments not including an optional CO$_2$ concentration module 470, CO$_2$-comprising gas from the industrial process 410 is fed from the removal module 420 to the CO$_2$ electrolysis module 430 via a conduit 422. In embodiments including an optional CO$_2$ concentration module 470, CO$_2$-comprising gas from the industrial process 410 is fed via a conduit 412 to one or more removal module 420 to remove and/or convert one or more constituent 428. The treated stream is then fed via a conduit 424 to an optional CO$_2$ concentration module 470 in order to increase the concentration of the CO$_2$ in the gas stream and remove one or more constituent 474. The CO$_2$-concentrated gas stream is then fed via a conduit 472 to a CO$_2$ electrolysis module 430 for conversion of at least a portion of the gas stream. At least a portion of the converted gas stream may be passed from the CO$_2$ electrolysis module 430 to the CO-consuming process 440 via a conduit 432. In some embodiments, the constituent 474 is CO and/or H$_2$, which is passed via conduit 476 to the CO-consuming process 440. In some embodiments, a water substrate is fed via a conduit 482 to an H$_2$ electrolysis module 480 for conversion of at least a portion of the water substrate, and an H$_2$-enriched stream is passed via a conduit 484 to the CO-consuming process 440. Optionally, at least a portion of O$_2$ may be fed from the H$_2$ electrolysis module 480 to the industrial process 410 via a conduit 486.

At least a portion of the gas stream from the CO$_2$ electrolysis module 430 may be passed to the industrial process 410 via conduit 436. In particular embodiments, the process includes an O$_2$ separation module 460 following the CO$_2$ electrolysis module 430 to separate at least a portion of O$_2$ from the gas stream. In embodiments including an O$_2$ separation module 460 following the CO$_2$ electrolysis module 430, the gas stream is fed via a conduit 434 from the CO$_2$ electrolysis module 430 to the O$_2$ separation module 460. In embodiments utilizing an O$_2$ separation module 460 after the CO$_2$ electrolysis module 430, at least a portion of the gas stream is fed from the O$_2$ separation module 460 to the industrial process 410 via a conduit 464. In embodiments utilizing an O$_2$ separation module 460 after the CO$_2$ electrolysis module 430, at least a portion of the O$_2$-lean stream is fed from the O$_2$ separation module 460 to the CO-consuming process via a conduit 462. In some embodiments utilizing an O$_2$ separation module 460 after the CO$_2$ electrolysis module 430, at least a portion of the O$_2$-lean stream is fed from the O$_2$ separation module 460 back to the CO$_2$ electrolysis module 430 via a conduit 466. In embodiments not utilizing an O$_2$ separation module 460, a portion of the gas stream may be fed from the CO$_2$ electrolysis module 430 to the industrial process 410 via a conduit 436.

In some embodiments, the CO-consuming process 440 of FIG. 4 comprises a CO$_2$-producing reaction step. In embodiments wherein a post-CO-consuming process gaseous substrate comprises $CO_2$, at least a portion of the post-CO-consuming process gaseous substrate is passed via a conduit 442 to one or more removal module 450 to remove and/or convert one or more constituent 458. The treated gas stream is then passed via a conduit 452 to a $CO_2$ electrolysis module 430 for conversion of at least a portion of the gas stream. In particular embodiments, the post-CO-consuming process gaseous substrate is passed via a conduit 442 to the same one or more removal module 420 that receives the $CO_2$-comprising gas from the industrial process 410. In various embodiments, the post-CO-consuming process gaseous substrate may be passed to the one or more removal module 420 that receives the $CO_2$-comprising gas from the industrial process 410 and the one or more removal module 450.

The CO-consuming process 440 of FIG. 4 may be a gas fermentation process and may occur in an inoculator and/or one or more bioreactors. For example, the CO-consuming process 440 may be a gas fermentation process in a bioreactor comprising a culture of at least one C1-fixing microorganism. In embodiments wherein the CO-consuming process 440 is a gas fermentation process, a culture may be fermented to produce one or more fermentation products 446 and a post-fermentation gaseous substrate (CO-consuming process gaseous substrate).

Figure 5:
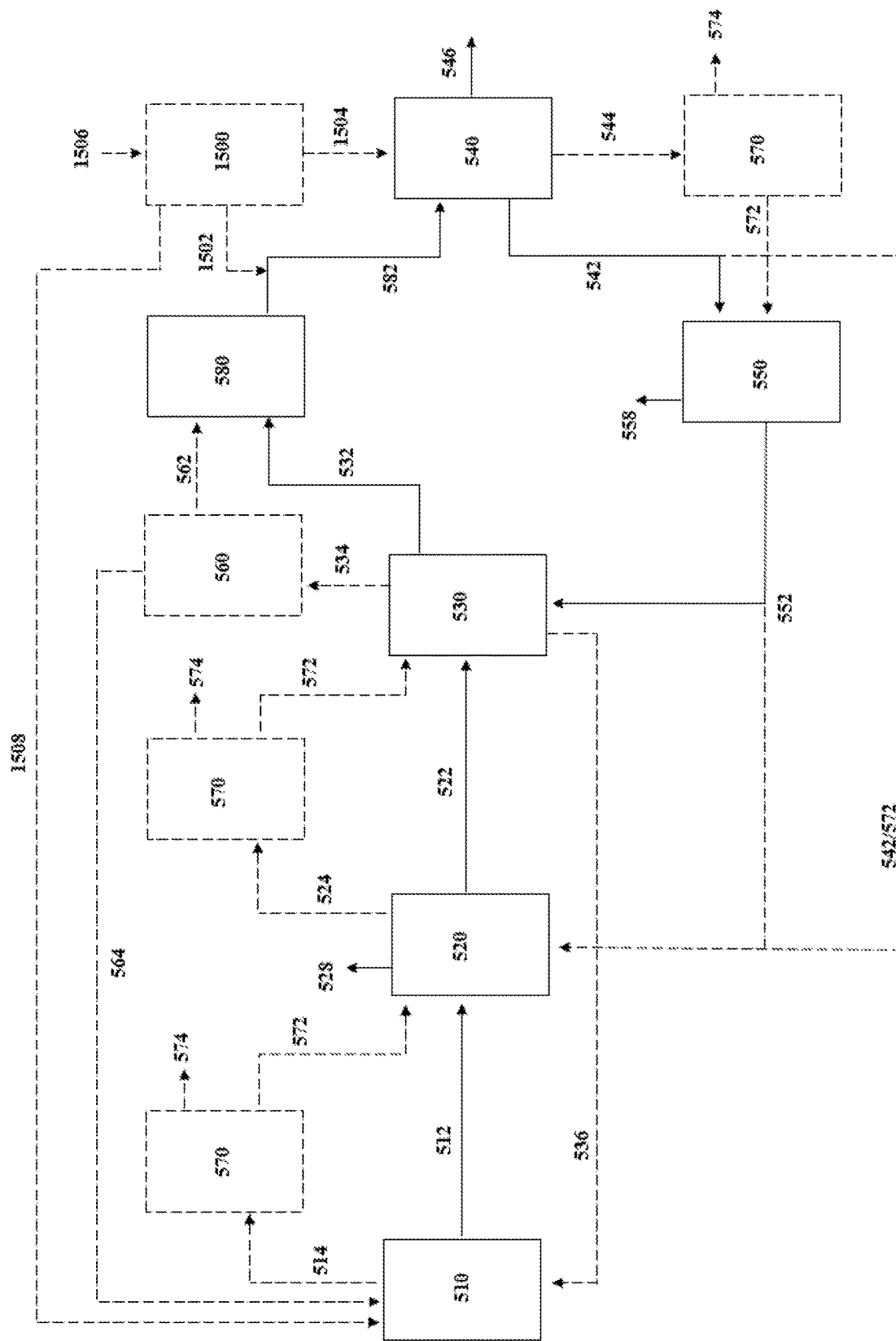
FIG. 5 shows a process integration scheme depicting integration of an $H_2$ electrolysis module following an optional pressure module, wherein a portion of the gas from the $H_2$ electrolysis module is blended with the gas from the $CO_2$ electrolysis module prior to being passed to the CO-consuming process.

FIG. 5 shows a process for integration of an industrial process 510 with a removal module 520, optional $CO_2$ concentration modules 570, a $CO_2$ electrolysis module 530, a CO-consuming process 540, an optional $O_2$ separation module 560, an optional pressure module 580, and an optional $H_2$ electrolysis module 1500, in accordance with one aspect of the invention. $CO_2$-comprising gas from the industrial process 510 is fed via a conduit 512 to one or more removal module 520 to remove and/or convert one or more constituent 528. The treated gas from the one or more removal module 520 is then fed via a conduit 522 to a $CO_2$ electrolysis module 530 for conversion of at least a portion of the gas stream. In embodiments that blend $H_2$, a hydrolysis electrolysis module 1500 may send an $H_2$-rich gas stream, via a conduit 1502, to be blended with the converted gas stream prior to the converted gas stream prior to the being introduced to the CO-consuming process 540.

In particular embodiments, the invention provides one or more pressure module 580 to increase the pressure of the converted gas from the $CO_2$ electrolysis module 530. In embodiments utilizing a pressure module 580 after the $CO_2$ electrolysis module 530, at least a portion of the gas stream is fed from the $CO_2$ electrolysis module 530 to the pressure module 580 via a conduit 532. The pressure module 580 increases the pressure of the gas stream and passes the gas stream to the CO-consuming process 540, via a conduit 582.

In various embodiments, the $H_2$ electrolysis module 1500 is incorporated with an $O_2$ separation module 560 and/or a pressure module 580. In various embodiments, a water substrate is fed via a conduit 1506 to the $H_2$ electrolysis module 1500, and the $H_2$ electrolysis module may send an $H_2$-rich gas stream, via a conduit 1502, to be blended with the converted gas stream prior to the gas stream being introduced to the CO-consuming process 540. In particular embodiments, the conduit 1502 for sending the $H_2$-rich gas stream is connected with the conduit 582 for sending the pressurized CO-rich stream to provide for blending of the streams. In various embodiments, the $H_2$ electrolysis module 1500 sends an $H_2$-rich gas stream directly to the CO-consuming process 540 via a conduit 1504. Optionally, at least a portion of $O_2$ may be fed from the $H_2$ electrolysis module 1500 to the industrial process 510 via a conduit 1508.

In certain embodiments, the invention integrates an industrial process 510, an optional $CO_2$ concentration module 570, a removal module 520, a $CO_2$ electrolysis module 530, an optional $O_2$ separation module 560, an optional pressure module 580, an $H_2$ electrolysis module 1500, and a CO-consuming process 540, in accordance with one aspect of the invention. $CO_2$-comprising gas from the industrial process 510 is fed via the conduit 514 to an optional $CO_2$ concentration module 570 to increase the concentration of the $CO_2$ in the gas stream and remove one or more constituent 574. The optional $CO_2$ concentration module 570 sends the gas to the removal module 520, via a conduit 572, to remove and/or convert one or more constituent 528. The treated stream is then fed via a conduit 524 to an optional $CO_2$ concentration module 570 to increase the concentration of the $CO_2$ in the gas stream and remove one or more constituent 574. The optional $CO_2$ concentration module 570 sends the gas, via a conduit 572, to a $CO_2$ electrolysis module 530 for conversion of at least a portion of the gas stream. At least a portion of the converted gas stream may be passed to an optional $O_2$ separation module 560, via a conduit 534, to separate at least a portion of $O_2$ from the gas stream. At least a portion of the $O_2$-rich gas stream may be passed from the optional $O_2$ separation module 560 to the industrial process 510, via a conduit 564. At least a portion of the $O_2$-rich gas stream may be fed from the $CO_2$ electrolysis module 530 to the industrial process 510 via a conduit 536. At least a portion of the $O_2$-depleted gas stream may be passed from the optional $O_2$ separation module 560 to an optional pressure module 580, via a conduit 562. The gas stream from the optional pressure module 580 is sent, via a conduit 582, to the CO-consuming process 540. The gas stream may be blended with an $H_2$-rich gas stream prior to being introduced to the CO-consuming process 540. Preferably, the $H_2$-rich gas stream is passed from an $H_2$ electrolysis module 1500 via a conduit 1502.

The CO-consuming process 540 of FIG. 5 produces a product 546. The CO-consuming process may be a gas fermentation process and may occur in an inoculator and/or one or more bioreactors. For example, the CO-consuming process may involve fermenting a culture to produce one or more fermentation product 546 and a post-fermentation gaseous substrate (post-CO-consuming process gaseous substrate). The post-CO-consuming process gaseous substrate may be passed via a conduit 542 to the removal module 550 to remove and/or convert one or more constituent 558. In embodiments including a $CO_2$ concentration module 570 after the CO-consuming process, the post-CO-consuming process gaseous substrate may be passed via a conduit 544 to an optional $CO_2$ concentration module 570 to increase the concentration of the $CO_2$ in the gas stream and remove one or more constituent 574. The optional $CO_2$ concentration module 570 may send the post-CO-consuming process gaseous substrate to the removal module 550, via a conduit 572, to remove and/or convert one or more constituent 558. The treated gas stream may then be passed via a conduit 552 to a $CO_2$ electrolysis module 530 for conversion of at least a portion of the gas stream. In particular embodiments, the post-CO-consuming process gaseous substrate is passed, via a conduit 542 to the same one or more removal module 520 that receives the $CO_2$-comprising gas from the industrial process 510. In various embodiments, the post-CO-consuming process gaseous substrate may be passed to both the one or more removal module 520 that receives the $CO_2$-comprising gas from the industrial process 510 and the one or more removal module 550.

The invention provides generally for the removal of constituents from the gas stream that may have adverse effects on downstream processes, for instance, the downstream fermentation process and/or downstream modules. In particular embodiments, the invention provides for one or more further removal module between the various modules in order to prevent the occurrence of such adverse effects.

In various instances, the conversion of a $CO_2$-comprising gaseous substrate by an $CO_2$ electrolysis module results in one or more constituent passing through the $CO_2$ electrolysis module 630. In various embodiments, this results in one or more constituent in the CO-enriched stream. In certain instances, the constituent includes portions of converted $O_2$. In various embodiments, the further removal module is a deoxygenation module for removing $O_2$ from the CO-enriched stream.

Figure 6:
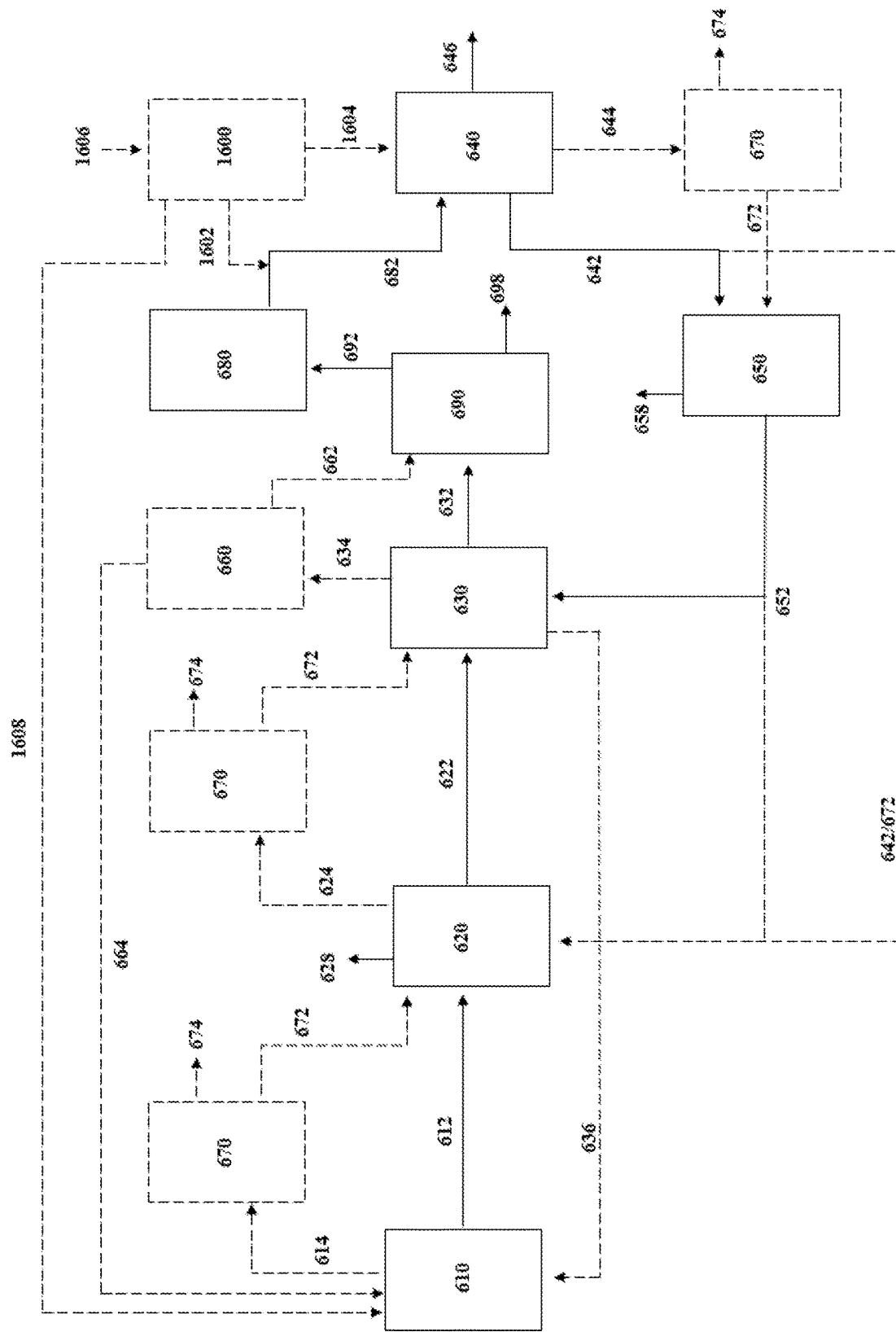
FIG. 6 shows a process integration scheme depicting integration of a further removal module following a $CO_2$ electrolysis module.

FIG. 6 shows the integration of a $CO_2$ electrolysis module 630, an optional $O_2$ separation module 660, an optional pressure module 680, with a further removal module 690. In certain instances, the further removal module 690 is utilized following the $CO_2$ electrolysis module 630. In embodiments utilizing a further removal module 690 after the $CO_2$ electrolysis module 630, at least a portion of the gas stream is fed from the $CO_2$ electrolysis module 630 to the further removal module 690 via a conduit 632. The further removal module 690 removes and/or converts one or more constituent 698 in the gas stream. Additionally, when utilizing an optional $O_2$ separation module 660, the $O_2$ separation module 660 sends the gas stream via a conduit 662 to the further removal module 690 to remove and/or convert one or more constituent 698. The treated stream is then fed, via a conduit 692, to an optional pressure module 680.

In certain embodiments, the invention integrates an industrial process 610, an optional $CO_2$ concentration module 670, a removal module 620, a $CO_2$ electrolysis module 630, a further removal module 690, an optional $O_2$ separation module 660, an optional pressure module 680, an optional $H_2$ electrolysis module 1600, and a CO-consuming process 640, in accordance with one aspect of the invention. In embodiments not including an optional $CO_2$ concentration module 670 between the industrial process 610 and the removal module 620, the $CO_2$-comprising gas from the industrial process 610 is fed via a conduit 612 to the removal module 620. In embodiments including an optional $CO_2$ concentration module 670 between the industrial process 610 and the removal module 620, the $CO_2$-comprising gas from the industrial process 610 is fed via the conduit 614 to an optional $CO_2$ concentration module 670 to increase the concentration of the $CO_2$ in the gas stream and remove one or more constituent 674. The optional $CO_2$ concentration module 670 sends the gas to the removal module 620, via a conduit 672, to remove and/or convert one or more constituent 628. In embodiments not including a $CO_2$ concentration module 670 between the removal module 620 and the $CO_2$ electrolysis module 630, the treated stream is fed via a conduit 622 from the removal module 620 to the $CO_2$ electrolysis module 630. In embodiments including a $CO_2$ concentration module 670 between the removal module 620 and the $CO_2$ electrolysis module 630, the treated stream is then fed via a conduit 624 to an optional $CO_2$ concentration module 670 to increase the concentration of the $CO_2$ in the gas stream and remove one or more constituent 674. The optional $CO_2$ concentration module 670 sends the gas, via a conduit 672, to a $CO_2$ electrolysis module 630 for conversion of at least a portion of the gas stream. At least a portion of the $O_2$-rich gas stream may be fed from the $CO_2$ electrolysis module 630 to the industrial process 610 via a conduit 636. At least a portion of the CO-rich gas stream may be passed via a conduit 632 to a further removal module 690 to remove and/or convert one or more constituent 698. At least a portion of the treated gas stream may be passed via a conduit 634 to an optional $O_2$ separation module 660 to separate at least a portion of $O_2$ from the gas stream. At least a portion of the $O_2$-rich gas stream may be passed via a conduit 664 from the optional $O_2$ separation module 660 to the industrial process 610. At least a portion of the gas stream may be passed from the optional $O_2$ separation module 660 via a conduit 662 to the further removal module 690 to remove and/or convert one or more constituent 698. At least a portion of the gas stream may be passed from the further removal module 690, via a conduit 692, to an optional pressure module 680. The gas stream from the optional pressure module 680 is sent, via a conduit 682, to the CO-consuming process 640. The gas stream may be blended with an $H_2$-rich gas stream prior to being introduced to the CO-consuming process 640. Preferably, a water substrate is passed via a conduit 1606 to an $H_2$ electrolysis module 1600, and an $H_2$-rich gas stream is passed from an $H_2$ electrolysis module 1600 via a conduit 1602. In various embodiments, the $H_2$ electrolysis module 1600 sends an $H_2$-rich gas stream directly to the CO-consuming process 640 via a conduit 1604. In some embodiments, $O_2$ produced by the $H_2$ electrolysis module 1600 is passed via conduit 1608 to the industrial process 610.

The CO-consuming process 640 of FIG. 6 may produce a product 646. The CO-consuming process may be a gas fermentation process and may occur in an inoculator and/or one or more bioreactors. For example, the CO-consuming process may involve fermenting a culture to produce one or more fermentation product 646 and a post-fermentation gaseous substrate (post-CO-consuming process gaseous substrate. The post-CO-consuming process gaseous substrate is passed via a conduit 644 to an optional $CO_2$ concentration module 670 to increase the concentration of the $CO_2$ in the gas stream and remove one or more constituent 674. The optional $CO_2$ concentration module 670 sends the post-CO-consuming process gaseous substrate to the removal module 650, via a conduit 672, to remove and/or convert one or more constituent 658. The treated gas stream is then passed via a conduit 652 to a $CO_2$ electrolysis module 630 for conversion of at least a portion of the gas stream. In particular embodiments, the post-CO-consuming process gaseous substrate is passed, via a conduit 642 to the same one or more removal module 620 that receives the $CO_2$-comprising gas from the industrial process 610. In various embodiments, the post-CO-consuming process gaseous substrate may be passed to the one or more removal module 620 that receives the $CO_2$-comprising gas from the industrial process 610 and the one or more removal module 650.

In various embodiments, the invention provides an integrated process comprising electrolysis wherein the power supplied for the electrolysis process is derived, at least in part, from a renewable energy source.

Although the substrate is typically gaseous, the substrate may also be provided in alternative forms. For example, the substrate may be dissolved in a liquid saturated with a CO-comprising gas using a microbubble dispersion generator. By way of further example, the substrate may be adsorbed onto a solid support.

The C1-fixing microorganism in a bioreactor is typically a carboxydotrophic bacterium. In particular embodiments, the carboxydotrophic bacterium is selected from the group comprising *Moorella, Clostridium, Ruminococcus, Acetobacterium, Eubacterium, Butyribacterium, Oxobacter, Methanosarcina, Methanosarcina*, and *Desulfotomaculum*. In various embodiments, the carboxydotrophic bacterium is *Clostridium autoethanogenum*.

All references, including publications, patent applications, and patents, cited herein are hereby incorporated by reference to the same extent as if each reference were individually and specifically indicated to be incorporated by reference and were set forth in its entirety herein. The reference to any prior art in this specification is not, and should not be taken as, an acknowledgement that that prior art forms part of the common general knowledge in the field of endeavour in any country.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. The term "consisting essentially of" limits the scope of a composition, process, or method to the specified materials or steps, or to those that do not materially affect the basic and novel characteristics of the composition, process, or method. The use of the alternative (i.e., "or") should be understood to mean either one, both, or any combination thereof of the alternatives. As used herein, the term "about" means±20% of the indicated range, value, or structure, unless otherwise indicated.

Recitation of ranges of values herein are merely intended to serve as a shorthand method of referring individually to each separate value falling within the range, unless otherwise indicated herein, and each separate value is incorporated into the specification as if it were individually recited herein. For example, any concentration range, percentage range, ratio range, integer range, size range, or thickness range is to be understood to include the value of any integer within the recited range and, when appropriate, fractions thereof (such as one tenth and one hundredth of an integer), unless otherwise indicated.

All methods described herein can be performed in any suitable order unless otherwise indicated herein or otherwise clearly contradicted by context. The use of any and all examples, or exemplary language (i.e., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A system comprising:
   a. an industrial system comprising a gaseous substrate output conduit in fluid communication with a removal module comprising a $CO_2$-treated gas stream output conduit;
   b. a $CO_2$ concentration module in fluid communication with the $CO_2$-treated gas stream output conduit and comprising a $CO_2$-concentrated gas stream output conduit;
   c. a $CO_2$ electrolysis module in fluid communication with the $CO_2$-concentrated gas stream output conduit and comprising a CO-enriched stream output conduit and a first $O_2$-enriched stream output conduit;
   d. an $O_2$ separation module in fluid communication with the first $O_2$-enriched stream output conduit and comprising a second $O_2$-enriched stream output conduit in fluid communication with the industrial system and an $O_2$-lean stream output conduit; and
   e. a bioreactor comprising a culture of at least one C1-fixing microorganism in fluid communication with the CO-enriched stream output conduit and the $O_2$-lean stream output conduit, wherein the bioreactor comprises a tail gas stream output conduit in fluid communication with the removal module and a fermentation products output conduit.

2. The system of claim 1, further comprising a first pressure module in fluid communication with the gaseous substrate output conduit and the removal module.

3. The system of claim 1, further comprising a second pressure module in fluid communication with the CO-enriched stream output conduit and the bioreactor.

4. The system of claim 1, further comprising a water electrolysis module in fluid communication with the bioreactor.

5. The system of claim 1, further comprising a third pressure module in fluid communication with the tail gas stream output conduit and the removal module.

6. The system of claim 1, wherein the industrial system carries out an industrial process selected from carbohydrate fermentation, cement making, pulp and paper making, steel making, oil refining and associated processes, petrochemical production, coke production, anaerobic or aerobic digestion, gasification, natural gas extraction, oil extraction, metallurgical processes, production and/or refinement of aluminum, copper, and/or ferroalloys, geological reservoirs, Fischer-Tropsch processes, methanol production, pyrolysis, steam methane reforming, dry methane reforming, partial oxidation of biogas or natural gas, autothermal reforming of biogas or natural gas, and any mixture thereof.

7. The system of claim 1, wherein the removal module is selected from a hydrolysis module, an acid gas removal module, a deoxygenation module, a catalytic hydrogenation module, a particulate removal module, a chloride removal module, a tar removal module, a hydrogen cyanide polishing module, or any combination thereof.

8. The system of claim 1, further comprising a deoxygenation module in fluid communication with the CO-enriched stream outlet conduit.

9. The system of claim 1, wherein the C1-fixing microorganism is a carboxydotrophic bacterium.

10. The system of claim 9, wherein the carboxydotrophic bacterium is selected from *Moorella, Clostridium, Ruminococcus, Acetobacterium, Eubacterium, Butyribacterium, Oxobacter, Methanosarcina*, and *Desulfotomaculum*.

11. The system of claim 10, wherein the carboxydotrophic bacterium is *Clostridium autoethanogenum*.

12. The system of claim 1, further comprising a conversion process system in fluid communication with the fermentation products output conduit, wherein the conversion process system is a diesel fuel component conversion process system, a jet fuel component conversion process system, and/or a gasoline fuel component conversion process system.

13. The system of claim 1 wherein the $O_2$-lean stream output conduit is further in fluid communication with the electrolysis module.

* * * * *